United States Patent
Fang et al.

(10) Patent No.: US 10,632,220 B2
(45) Date of Patent: Apr. 28, 2020

(54) BIOLOGICAL INDICATOR WITH VARIABLE RESISTANCE

(71) Applicant: ASP Global Manufacturing GmbH, Schaffhausen (CH)

(72) Inventors: Yan Fang, Irvine, CA (US); Griffith E. Altmann, Ladera Ranch, CA (US); Behnam Amin, Mission Viejo, CA (US); Jeremy Yarwood, Aliso Viejo, CA (US); Lawrence Y. Mok, Hacienda Heights, CA (US)

(73) Assignee: ASP GLOBAL MANUFACTURING GMBH, Schaffhausen (CH)

( * ) Notice: Subject to any disclaimer, the term of this patent is extended or adjusted under 35 U.S.C. 154(b) by 180 days.

(21) Appl. No.: 15/265,910

(22) Filed: Sep. 15, 2016

(65) Prior Publication Data

US 2018/0071421 A1 Mar. 15, 2018

(51) Int. Cl.
*A61L 2/28* (2006.01)
*A61L 2/24* (2006.01)
(Continued)

(52) U.S. Cl.
CPC .................... *A61L 2/28* (2013.01); *A61L 2/16* (2013.01); *A61L 2/202* (2013.01); *A61L 2/208* (2013.01); *A61L 2/24* (2013.01); *A61L 2202/14* (2013.01)

(58) Field of Classification Search
CPC . A61L 2/28; A61L 2/202; A61L 2/208; A61L 2/24; A61L 2/16
See application file for complete search history.

(56) References Cited

U.S. PATENT DOCUMENTS 6,325,972 B1 12/2001 Jacobs et al.
6,365,102 B1  4/2002 Wu et al.
(Continued)

FOREIGN PATENT DOCUMENTS

EP 1 308 175 A1 5/2003
EP 2 340 853 A1 7/2011
(Continued)

OTHER PUBLICATIONS

U.S. Appl. No. 62/316,722, filed Apr. 1, 2016.
(Continued)

*Primary Examiner* — Regina M Yoo
(74) *Attorney, Agent, or Firm* — Frost Brown Todd LLC

(57) ABSTRACT

A biological indicator with variable resistance may be controlled by moving a cap or housing of the biological indicator to cause the size of vents that allow flow of sterilant through the housing to decrease or increase in effective size. An indicator window may show a user the current resistance of the biological indicator, and may also show a readable indicator that may be captured by a scanner to allow a sterilizing cabinet to identify the current resistance. When the level of resistance shown by the readable indicator is not compatible with a sterilization cycle selected by a user, the procedure may be delayed and a notification provided to the user that a problem exists. The readable indicator may be a passive tag with a memory that allows information to be read and written, so that the biological indicator may carry data from one device to another.

19 Claims, 13 Drawing Sheets

(51) Int. Cl.
*A61L 2/16* (2006.01)
*A61L 2/20* (2006.01)

(56) References Cited

U.S. PATENT DOCUMENTS

| | | |
|---|---|---|
| 6,447,719 B1 | 9/2002 | Agamohamadi et al. |
| 6,485,979 B1 * | 11/2002 | Kippenhan ............... A61L 2/24 422/403 |
| 6,852,277 B2 | 2/2005 | Platt et al. |
| 6,852,279 B2 | 2/2005 | Williams et al. |
| 6,939,519 B2 | 9/2005 | Agamohamadi et al. |
| 8,333,933 B2 | 12/2012 | Oshiro et al. |
| 2003/0087441 A1 * | 5/2003 | Lemus ..................... C12Q 1/22 436/1 |
| 2017/0252472 A1 * | 9/2017 | Dang ........................ A61L 2/04 |

FOREIGN PATENT DOCUMENTS

| | | |
|---|---|---|
| EP | 3 213 774 A1 | 9/2017 |
| WO | WO 2016/057520 A1 | 4/2016 |

OTHER PUBLICATIONS

U.S. Appl. No. 62/376,517, filed Aug. 18, 2016.
U.S. Appl. No. 15/057,768, filed Mar. 1, 2016.
European Search Report and Written Opinion dated Mar. 1, 2018 for Application No. EP 17191203.3, 7 pgs.

* cited by examiner

BIOLOGICAL INDICATOR WITH VARIABLE RESISTANCE

BACKGROUND

Re-usable medical devices such as certain surgical instruments, endoscopes, etc., may be sterilized before re-use in order to minimize the likelihood that a contaminated device might be used on a patient, which could cause an infection in the patient. Various sterilization techniques may be employed, such as steam, hydrogen peroxide, peracetic acid, and vapor phase sterilization, either with or without a gas plasma and ethylene oxide (EtO). Each of these methods may depend to a certain extent on the diffusion rates of the sterilization fluids (e.g., gases) upon or into the medical devices to be sterilized.

Before sterilization, medical devices may be packaged within containers or pouches having a semi-permeable barrier that allows transmission of the sterilizing fluid—sometimes referred to as a sterilant—but prevents admission of contaminating organisms, particularly post-sterilization and until the package is opened by medical personnel. For the sterilization cycle to be efficacious, the contaminating organisms within the package must be killed because any organisms that survive the sterilization cycle could multiply and re-contaminate the medical device. Diffusion of the sterilant may be particularly problematic for medical devices that have diffusion-restricted spaces therein because these diffusion-restricted spaces may reduce the likelihood that a sterilization cycle may be effective. For example, some endoscopes have one or more long narrow lumens into which the sterilant must diffuse in sufficient concentration for sufficient time to achieve a successful sterilization cycle.

Sterilization of medical devices may be performed with an automated sterilization system such as a STERRAD® System by Advanced Sterilization Products of Irvine, Calif. Examples of automated sterilization systems are described in U.S. Pat. No. 6,939,519, entitled "Power System for Sterilization Systems Employing Low Frequency Plasma," issued Sep. 6, 2005, the disclosure of which is incorporated by reference herein; U.S. Pat. No. 6,852,279, entitled "Sterilization with Temperature-Controlled Diffusion Path," issued Feb. 8, 2005, the disclosure of which is incorporated by reference herein; U.S. Pat. No. 6,852,277, entitled "Sterilization System Employing a Switching Module Adapter to Pulsate the Low Frequency Power Applied to a Plasma," issued Feb. 8, 2005, the disclosure of which is incorporated by reference herein; U.S. Pat. No. 6,447,719, entitled "Power System for Sterilization Systems Employing Low Frequency Plasma," issued Sep. 10, 2002, the disclosure of which is incorporated by reference herein; and U.S. Provisional Pat. App. No. 62/316,722, entitled "System and Method for Sterilizing Medical Devices," filed Apr. 1, 2016, the disclosure of which is incorporated by reference herein.

Operator error may result in medical devices that are erroneously believed to be decontaminated being returned to service. Confirming that a sterilization cycle has been efficacious may help medical personnel avoid using a contaminated medical device on a patient. The sterilized medical device might not itself be checked for contaminating organisms because such an activity may introduce other contaminating organisms to the medical device, thereby re-contaminating it. Thus, an indirect check may be performed using a sterilization indicator. A sterilization indicator is a device that may be placed alongside or in proximity to a medical device being subject to a sterilization cycle, such that the sterilization indicator is subject to the same sterilization cycle as the medical device. For instance, a biological indictor having a predetermined quantity of microorganisms may be placed into a sterilization chamber alongside a medical device and subject to a sterilization cycle. After the cycle is complete, the microorganisms in the biological indicator may be cultured to determine whether any of the microorganisms survived the cycle. The presence or absence of living microorganisms in the biological indicator will indicate whether the sterilization cycle was effective.

In view of the foregoing, it may be desirable to provide a sterilization system that minimizes opportunities for operator error, thereby maximizing the likelihood of successful sterilization cycles, thereby minimizing the risk of patient infection. While a variety of systems and methods have been made and used for medical device sterilization, it is believed that no one prior to the inventor(s) has made or used the technology as described herein.

BRIEF DESCRIPTION OF THE DRAWINGS

It is believed the present invention will be better understood from the following description of certain examples taken in conjunction with the accompanying drawings, in which like reference numerals identify the same elements and in which.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. OVERVIEW OF EXEMPLARY STERILIZATION SYSTEM

Figure 1:
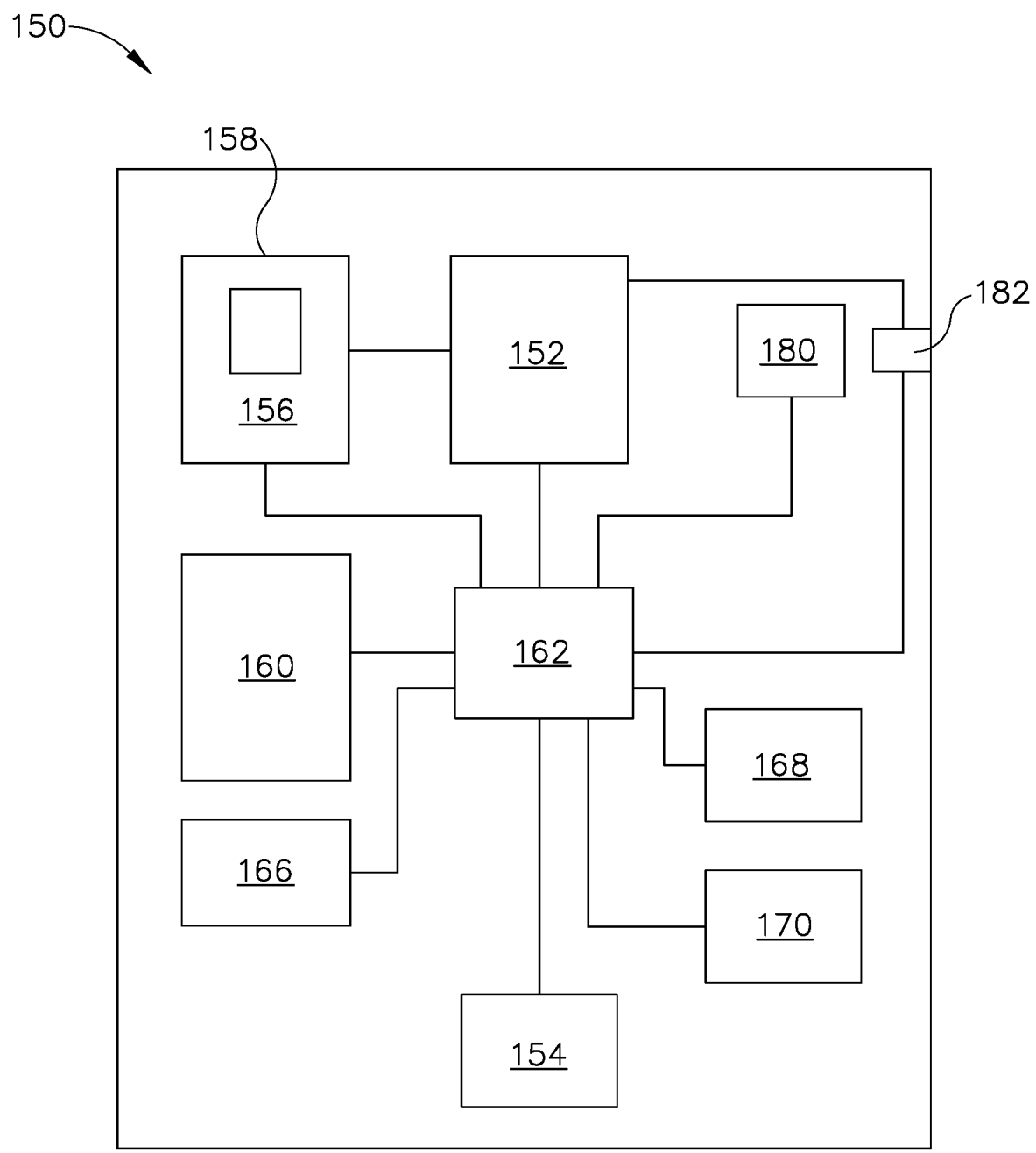
FIG. 1 depicts a schematic view of an exemplary medical device sterilizing cabinet.

FIG. 1 depicts an exemplary sterilizing cabinet (150) that is operable to sterilize medical devices such as endoscopes, etc. Sterilizing cabinet (150) of the present example includes a sterilization chamber (152), which is configured to receive one or more medical devices for sterilization. While not shown, sterilizing cabinet (150) also includes a door that opens and closes sterilization chamber (152) in response to actuation of a kick plate. An operator may thereby open and close sterilization chamber (152) in a hands-free fashion. Of course, any other suitable features may be used to provide selective access to sterilization chamber. Sterilizing cabinet (150) also includes a sterilization module (156) that is operable to dispense a sterilant into sterilization chamber (152) in order to sterilize medical devices contained in sterilization chamber (152). In the present example, sterilization module (156) is configured to receive replaceable sterilant cartridges (158) containing a certain amount of sterilant. By way of example only, each sterilant cartridge (158) may contain enough sterilant to perform five sterilization procedures.

In the present example, sterilization module (156) is operable to apply a sterilant in the form of a vapor within sterilization chamber (152). By way of example only, sterilization module (156) may comprise a combination of a vaporizer and a condenser. The vaporizer may include a chamber that receives a particular concentration of sterilant solution (e.g., a liquid hydrogen peroxide solution with a concentration of approximately 59% nominal, or between approximately 58% and approximately 59.6%); where the sterilant solution changes phase from liquid to vapor. The condenser may provide condensation of the sterilant solution vapor, and the concentration of the sterilant solution may be thereby increased (e.g., from approximately 59% nominal to somewhere between approximately 83% nominal and approximately 95% nominal), by removal of water vapor. Alternatively, any other suitable methods and components may be used to apply sterilant in the form of a vapor within sterilization chamber (152). In any case, to supplement the application of the sterilant in the form of a vapor, the sterilant may also be applied (in liquid form) to the inside of lumen(s) and/or other internal spaces within the medical device and/or the outside of the medical device, before the medical device is placed in sterilization chamber (152). In such versions, the sterilant may evaporate while a vacuum is applied to sterilization chamber (152) (e.g., as described in greater detail below with reference to block 310 of FIG. 3) and even after vacuum is applied; and provide more concentration of sterilant to the areas of the medical device with less penetration range, thereby further promoting effective sterilization.

Sterilizing cabinet (150) of the present example further includes a touch screen display (160). Touch screen display (160) is operable to render the various user interface display screens, such as those described in U.S. Provisional Pat. App. No. 62/316,722, the disclosure of which is incorporated by reference herein. Of course, touch screen display (160) may display various other screens as well. Touch screen display (160) is further configured to receive user input in the form of the user contacting touch screen display (160) in accordance with conventional touch screen technology. In addition, or in the alternative, sterilizing cabinet (150) may include various other kinds of user input features, including but not limited to buttons, keypads, keyboards, a mouse, a trackball, etc.

Sterilizing cabinet (150) of the present example further includes a processor (162), which is in communication with sterilization module (156) and with touch screen display (160). Processor (162) is operable to execute control algorithms to drive sterilization module (156) in accordance with user input. Processor (162) is further operable to execute instructions to display the various screens on touch screen display (160); and to process instructions received from a user via touch screen display (160) (and/or via other user input features). Processor (162) is also in communication with various other components of sterilization cabinet (150) and is thereby operable to drive those components and/or process input and/or other data from those components. Various suitable components and configurations that may be used to form processor (162) will be apparent to those of ordinary skill in the art in view of the teachings herein.

Sterilizing cabinet (150) of the present example further includes a communication module (154). Communication module (154) is configured to enable bidirectional communication between sterilizing cabinet (150) and a communication hub (not shown), a server, and/or other equipment. In some versions, communication module (154) is configured to communicate with a hub in accordance with at least some of the teachings of U.S. Patent App. No. 62/376,517, entitled "Apparatus and Method to Link Medical Device Sterilization Equipment," filed Aug. 18, 2016, the disclosure of which is incorporated by reference herein. By way of example only, communication module (154) may be configured to provide wired and/or wireless communication via as Ethernet, Wi-Fi, Bluetooth, USB, infrared, NFC, and/or other technologies. Various suitable components and configurations that may be used to form communication module (154) will be apparent to those of ordinary skill in the art in view of the teachings herein. Communications that are sent from or received through communication module (154) are processed through processor (162).

Sterilizing cabinet (150) of the present example further includes an identification tag reader (166), which is operable to read an identification tag of a biological indicator as described herein. By way of example only, identification tag reader (166) may comprise an optical reader that is operable to read an optical identification tag (e.g., barcode, data matrix code, QR code, etc.) of a biological indicator. In addition, or in the alternative, identification tag reader (166) may comprise an RFID reader that is operable to read an RFID identification tag of a biological indicator. In some versions where identification tag reader (166) comprises an RFID reader, identification tag reader (166) is also operable to write information to an RFID tag of a biological indicator. Various suitable components and configurations that may be used to form identification tag reader (166) will be apparent to those of ordinary skill in the art in view of the teachings herein. Data received through identification tag reader (166) is processed through processor (162).

Sterilizing cabinet (150) of the present example further includes a memory (168), which is operable to store control logic and instructions and that are executed by processor (162) to drive components such as sterilization module (156), touch screen display (160), communication module (154), and identification tag reader (166). Memory (168) may also be used to store results associated with setup of a sterilization cycle, performance of a load conditioning cycle, performance of a sterilization cycle, and/or various other kinds of information. Various suitable forms that memory (168) may take, as well as various ways in which memory (168) may be used, will be apparent to those of ordinary skill in the art in view of the teachings herein.

Sterilizing cabinet (150) of the present example further includes a printer (170), which is operable to print information such as results associated with setup of a sterilization cycle, performance of a load conditioning cycle, performance of a sterilization cycle, and/or various other kinds of information. By way of example only, printer (170) may comprise a thermal printer, though of course any other suitable kind of printer may be used. Various suitable forms that printer (170) may take, as well as various ways in which printer (170) may be used, will be apparent to those of ordinary skill in the art in view of the teachings herein. It should also be understood that printer (170) is merely optional and may be omitted in some versions.

Sterilizing cabinet (150) of the present example further includes a vacuum source (180) and a venting valve (182). Vacuum source (180) is in fluid communication with sterilization chamber (152) and is also in communication with processor (162). Thus, processor (162) is operable to selectively activate vacuum source (180) in accordance with one or more control algorithms. When vacuum source (180) is activated, vacuum source (180) is operable to reduce the pressure within sterilization chamber (152) as will be described in greater detail below. Venting valve (182) is also in fluid communication with sterilization chamber (152). In addition, venting valve (182) is in communication with processor (162) such that processor (162) is operable to selectively activate venting valve (182) in accordance with one or more control algorithms. When venting valve (182) is activated, venting valve (182) is operable to vent sterilization chamber (152) to atmosphere as will be described in greater detail below. Various suitable components that may be used to provide vacuum source (180) and venting valve (182) will be apparent to those of ordinary skill in the art in view of the teachings herein.

In addition to the foregoing, sterilizing cabinet (150) may be configured and operable in accordance with at least some of the teachings of U.S. Pat. No. 6,939,519, the disclosure of which is incorporated by reference herein; U.S. Pat. No. 6,852,279, the disclosure of which is incorporated by reference herein; U.S. Pat. No. 6,852,277, the disclosure of which is incorporated by reference herein; U.S. Pat. No. 6,447,719, the disclosure of which is incorporated by reference herein; U.S. Pat. No. 6,365,102, the disclosure of which is incorporated by reference herein; U.S. Pat. No. 6,325,972, the disclosure of which is incorporated by reference herein; and/or U.S. Provisional Patent App. No. 62/316,722, the disclosure of which is incorporated by reference herein.

II. OVERVIEW OF EXEMPLARY STERILIZATION PROCESS

Figure 2:
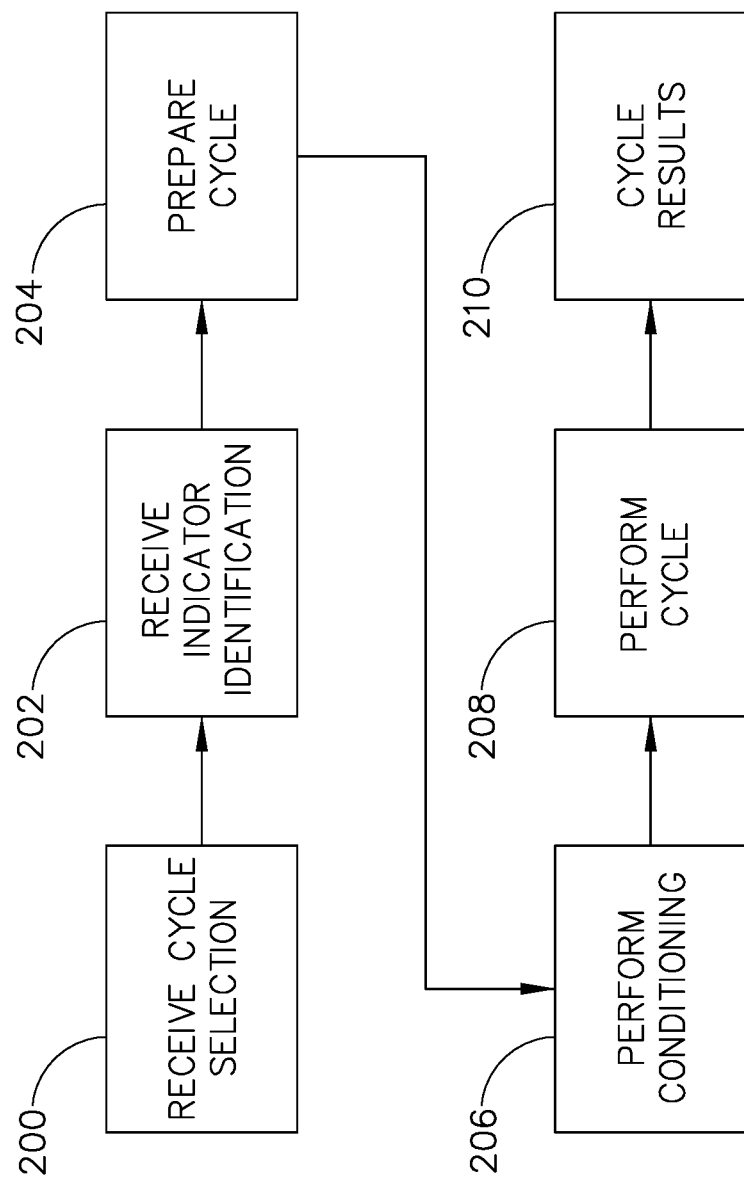
FIG. 2 depicts a high level flowchart of an exemplary set of steps that a sterilizing cabinet of the system of FIG. 1 could perform to sterilize a medical device.

FIG. 2 depicts a high level flowchart of an exemplary set of steps that sterilizing cabinet (150) could perform to sterilize a used medical device, such as an endoscope. Sterilizing cabinet (150) may be configured to perform one or more sterilization cycles, with different sterilization cycles being appropriate for different types and quantities of medical devices. Thus, as an initial step, sterilizing cabinet (150) may display one or more available sterilization cycles via touch screen display (160) and then receive a sterilization cycle selection (block 200) from the user.

Sterilizing cabinet (150) may also display instructions indicating whether a biological indicator should be used with the selected sterilization cycle, and receive a biological indicator identification (block 202). Such a biological indicator identification (block 202) may be provided via identification tag reader (166), via touch screen display (160), or otherwise. A biological indicator may be placed inside sterilization chamber (152) of sterilizing cabinet (150) before the sterilization cycle begins and may remain in the sterilization chamber during the sterilization cycle. The user may thus identify the particular biological indicator (block 202) before the biological indicator is placed in the sterilization chamber. The biological indicator may contain microorganisms that are responsive to a particular sterilization cycle. Upon completion of the sterilization cycle, the biological indicator may be tested for the microorganisms in order to provide a measure of the effectiveness of the sterilization cycle. A biological indicator may not necessarily be required for all sterilization cycles, but may be required based on hospital rules or local regulations.

Selection of a sterilization cycle (block 200) and identification of a biological indicator (block 202) may define one or more requirements for the configuration and arrangement of medical devices within sterilization chamber (152). Thus, in order to provide preparation for the sterilization cycle (block 204) once the sterilization cycle has been selected (block 200) and the biological indicator has been identified (block 202), sterilizing cabinet (150) may provide a display via touch screen display (160) indicating a proper medical device placement. This display may serve as a visual guide to a user's placement of medical device(s) (and perhaps a biological indicator) within sterilizing chamber (152) of sterilizing cabinet (150), based on the sterilization cycle selection (block 200). A door of sterilization chamber (152) may be opened to enable the user to place the medical device(s) (and perhaps a biological indicator) within sterilizing chamber (152) as instructed.

Once the user has placed the medical device in sterilizing chamber (152) based on these instructions, the user may press a start button or other button indicating that medical device placement is complete. In some versions, sterilizing cabinet (150) is configured to automatically verify proper medical device placement. By way of example only, sterilizing cabinet (150) may employ photo sensors, imaging devices, weight sensors, and/or other components to verify proper medical device placement in sterilizing chamber (152). It should be understood, however, that some versions of sterilizing cabinet (150) may lack the capability of automatically verifying proper placement of a medical device within sterilizing chamber (152).

If medical device placement is verified and/or the user has otherwise completed the cycle preparation (block 204), sterilizing cabinet (150) may start a load conditioning process (block 206). The load conditioning process (block 206) prepares sterilization chamber (152) and the medical device (s) within sterilization chamber (152) for optimal sterilization during a sterilization cycle. Conditioning may include controlling and optimizing one or more characteristics of sterilization chamber (152). For example, during load conditioning, sterilizing cabinet (150) may continuously monitor the level of moisture within sterilization chamber (152) while reducing the level of moisture by, for example, circulating and dehumidifying the air of sterilization chamber (152), creating a vacuum within sterilization chamber (152), heating sterilization chamber (152), and/or other methods for dehumidifying a sealed chamber. This may continue until sterilizing cabinet (150) determines that an acceptable level of moisture has been reached.

As part of the load conditioning cycle (block 206), sterilizing cabinet (150) may also continuously detect the temperature within sterilization chamber (152) while heating sterilization chamber (152) by, for example, convection of heated air, conduction through an interior surface of sterilization chamber (152), and/or using other techniques. This may continue until sterilizing cabinet (150) determines that an acceptable internal temperature has been reached. Various conditioning actions such as controlling temperature or humidity may be performed in parallel or in sequence. It should also be understood that the load conditioning cycle (block 206) may verify that the sterilization chamber is sealed; verifying contents of the sterilization chamber; checking physical characteristics of the contents of the sterilization chamber such as content volume, content weight, or other characteristics; and/or performing one or more conditioning steps that may include chemical treatment, plasma treatment, or other types of treatment to reduce moisture, raise temperature, and/or otherwise prepare the medical devices in sterilization chamber (152) for the sterilization cycle (block 208).

While the one or more conditioning actions are being performed as part of the load conditioning cycle (block 206), sterilizing cabinet (150) may display information via touch screen display (160) indicating to a user the duration of time before the sterilization cycle (block 208) performance may begin. Once all load conditioning criteria have been successfully met, the load conditioning cycle (block 206) is complete, and the sterilization cycle (block 208) may then be performed. It should therefore be understood that sterilizing cabinet (150) is configured such that the sterilization cycle (block 208) is not actually initiated until after the load conditioning cycle (block 206) is complete. It should also be understood that the load conditioning cycle (block 206) may be omitted or varied in some versions of sterilizing cabinet (150) operation.

As noted above, sterilization cabinet (150) may begin performing the sterilization cycle (block 208) automatically and immediately after load conditioning (block 206) has been completed. The sterilization cycle (block 208) may include exposing the medical device(s) in the sterilizing chamber to pressurized sterilant gas, further heat treatment, chemical treatment, plasma treatment, vacuum treatment, and/or other types of sterilization procedures. During performance of the sterilization cycle (block 208), sterilization cabinet (150) may display information via touch screen display (160) such as a duration remaining for the sterilization cycle (block 208), the current stage of the sterilization cycle (block 208) (e.g. plasma, vacuum, injection, heat, chemical treatment), and/or other information.

Figure 3:
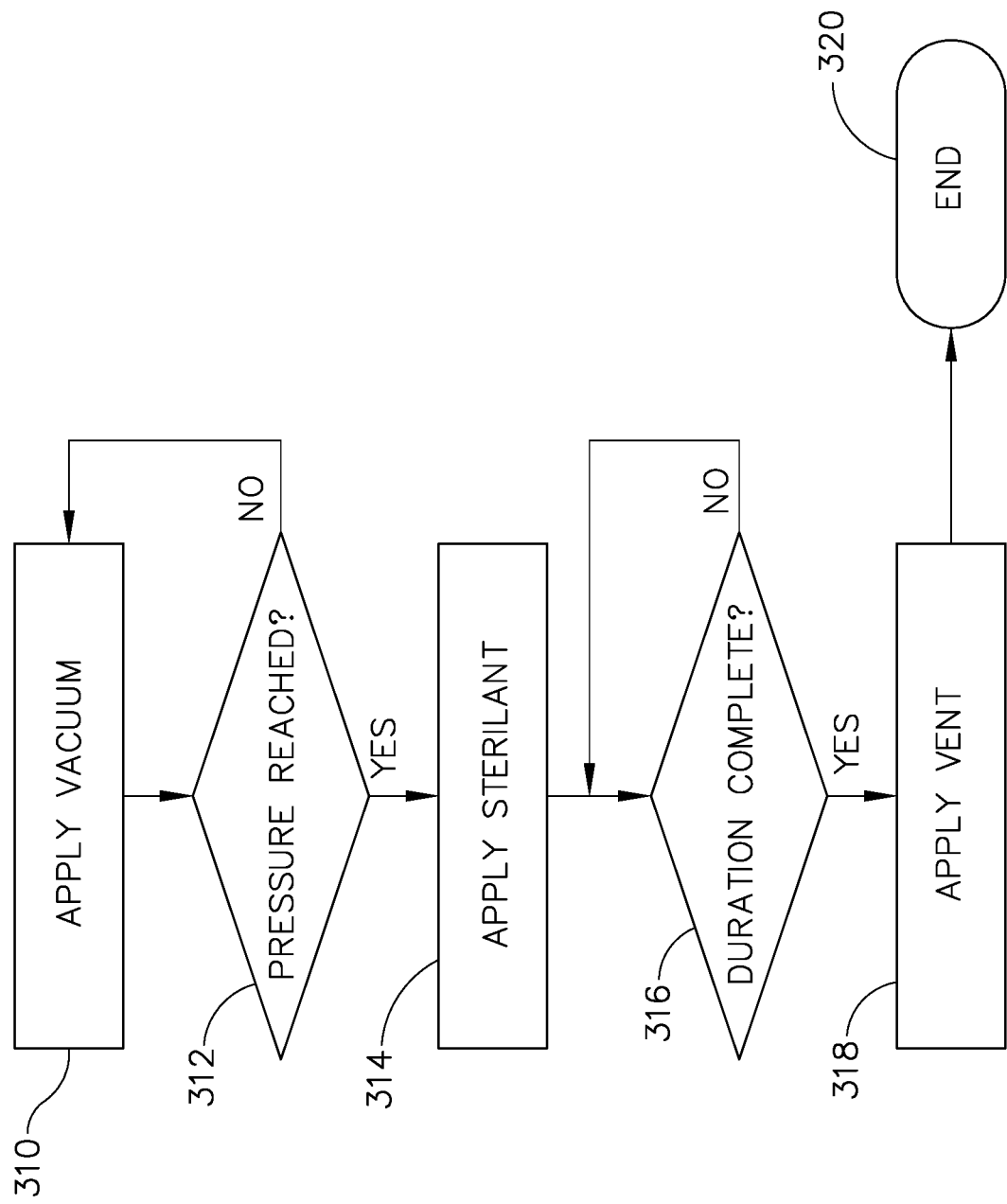
FIG. 3 depicts a flowchart of an exemplary set of steps that may be carried out as part of a sterilization cycle within the set of steps of FIG. 2.

In some versions, the sterilization cycle (block 208) includes the exemplary sub-steps shown in FIG. 3. In particular, the cycle may begin with a vacuum being applied (block 310) within sterilization chamber (152). In order to provide such a vacuum, processor (162) may activate vacuum source (180) in accordance with a control algorithm. Processor (162) will then determine (block 312) whether a sufficient pressure level has been reached within sterilization chamber (152). By way of example only, processor (162) may monitor data from one or more pressure sensors within sterilization chamber (152) as part of the determination step (block 312). Alternatively, processor (162) may simply activate vacuum source (180) for a predetermined time period and assume that the appropriate pressure has been reached in sterilization (152) based upon the duration for which vacuum source (180) is activated. Other suitable ways in which processor (162) may determine (block 312) whether a sufficient pressure level has been reached within sterilization chamber (152) will be apparent to those of ordinary skill in the art in view of the teachings herein. Until the appropriate pressure level has been reached within sterilization chamber (152), vacuum source (180) will remain activated.

Once sterilization chamber (152) reaches an appropriate pressure level (e.g., between approximately 0.2 torr and approximately 10 torr), processor (162) then activates sterilization module (156) to apply a sterilant (block 314) in sterilization chamber (152). This stage of the process may be referred to as the "transfer phase." By way of example only, the sterilant may comprise a vapor of oxidizing agent such as hydrogen peroxide, peroxy acids (e.g. peracetic acid, performic acid, etc.), ozone, or a mixture thereof. Furthermore, the sterilant may comprise chlorine dioxide. Various other suitable forms that the sterilant may take are described herein; while other forms will be apparent to those of ordinary skill in the art in view of the teachings herein. It should also be understood that, in some versions, the sterilant may be applied (block 314) in different ways based on the user's selection of cycle (block 200) as described above.

Once the sterilant has been applied (block 314) to sterilization chamber (152), processor (162) monitors the time (block 316) to determine whether a sufficient, predetermined duration has passed. By way of example only, this predetermined duration may be anywhere from a few seconds to several minutes. Until the predetermined duration has passed, sterilization chamber (152) remains in a sealed state at the above-noted predetermined pressure level, with the applied sterilant acting upon the medical device(s) contained within sterilization chamber (152).

After the predetermined duration has passed, processor (162) activates (block 318) venting valve (182) to vent sterilization chamber (152) to atmosphere. In some versions, sterilization chamber (152) is allowed to reach atmospheric pressure, while in other versions sterilization chamber (152) only reaches sub-atmospheric pressure. The venting stage of the process may be referred to as the "diffusion phase." In the present example, the sterilization cycle is then complete (block 320) after completion of the diffusion phase. In some other instances, vacuum is again applied to sterilization chamber (152) after completion of the diffusion phase; and then a plasma is applied to sterilization chamber (152), It should be understood that the entire sterilization cycle shown in FIG. 3 (including the above-noted variation where a subsequent vacuum then sterilization are applied) may be repeated one or more times after being completed once. In other words, a medical device may remain within sterilization chamber (152) and experience two or more iterations of the entire cycle shown in FIG. 3 (including the above-noted variation where a subsequent vacuum then sterilization are applied). The number of iterations may vary based on the cycle selection (block 200), which may be influenced by the particular kind of medical device that is being sterilized in sterilization chamber (152).

Upon completion of the sterilization cycle (block 208), sterilization cabinet (150) may cycle the results (block 210) of the sterilization cycle (block 208). For instance, if the sterilization cycle (block 208) was canceled or unable to complete due to error or by a user action, sterilizing cabinet (150) may remain sealed and may also display a sterilization cycle cancellation message via touch screen display (160); as well as various details relating to the sterilization cycle, such as date, time, configuration, elapsed time, sterilization cycle operator, the stage at which the sterilization cycle failed, and other information that may be used to identify why the sterilization cycle. If the sterilization cycle (block 208) is completed successfully, sterilization cabinet (150) may display a notification via touch screen display (160) indicating successful completion of the sterilization cycle (block 208). In addition, sterilization cabinet (150) may display information such as sterilization cycle identifier, sterilization cycle type, start time, duration, operator, and other information (666).

In some variations, a pre-plasma may be applied in the sterilization cycle (block 208) to heat up the medical device contained in sterilization chamber (152). By way of example only, plasma may be applied between applying a vacuum (block 310) and applying sterilant (block 314). In addition, or in the alternative, a post-plasma may be applied at the end of the sterilization cycle (block 208) to degrade any residual sterilant that may be adsorbed to the surface of the medical device contained in sterilization chamber (152). It should be understood that, before applying the post-plasma, a vacuum would first need to be applied to sterilization chamber (152).

By way of example only, the process depicted in FIG. 3 may be carried out at temperatures where the walls of sterilization chamber (152) are between approximately 30° C. and approximately 56° C., or more particularly between approximately 47° C. and approximately 56° C., or even more particularly approximately 50° C.; and where the temperature of the medical device in sterilization chamber (152) is between approximately 5-10° C. and approximately 40-55° C.

In addition to the foregoing, sterilizing cabinet (150) may be configured to perform sterilization processes in accordance with at least some of the teachings of U.S. Pat. No. 6,939,519, the disclosure of which is incorporated by reference herein; U.S. Pat. No. 6,852,279, the disclosure of which is incorporated by reference herein; U.S. Pat. No. 6,852,277, the disclosure of which is incorporated by reference herein; U.S. Pat. No. 6,447,719, the disclosure of which is incorporated by reference herein; U.S. Pat. No. 6,365,102, the disclosure of which is incorporated by reference herein; U.S. Pat. No. 6,325,972, the disclosure of which is incorporated by reference herein; and/or U.S. Provisional Patent App. No. 62/316,722, the disclosure of which is incorporated by reference herein.

While the foregoing examples are described in the context of sterilizing medical devices, and particularly endoscopes, it should be understood that the teachings herein may also be readily applied in the context of sterilizing various other kinds of articles. The teachings are not limited to endoscopes or other medical devices. Other suitable articles that may be sterilized in accordance with the teachings herein will be apparent to those of ordinary skill in the art.

III. EXEMPLARY BIOLOGICAL INDICATOR ASSEMBLY

Figure 4:
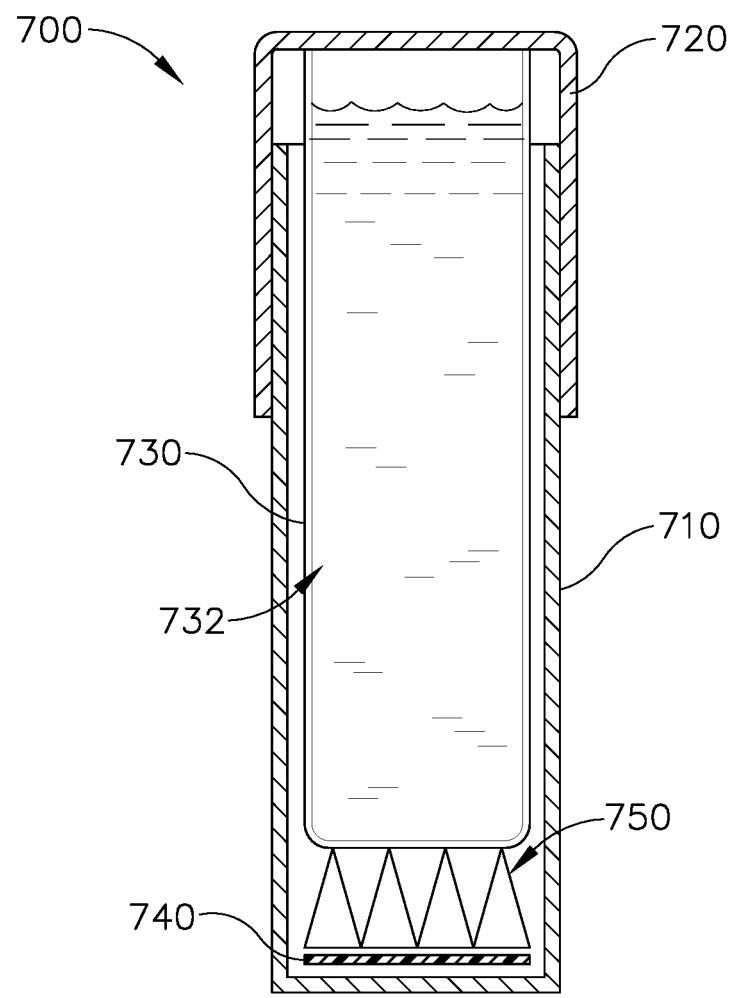
FIG. 4 depicts a schematic view of an exemplary biological indicator assembly that may be placed with a medical device in the sterilizing cabinet of FIG. 1.

As noted above, a biological indicator may be included in sterilizing cabinet (150) along with the medical device during the sterilization process (block 208) in order to ensure that the sterilization process (block 208) was successful. FIG. 4 shows an exemplary form that such a biological indicator may take. In particular, FIG. 4 shows a biological indicator (700) that includes a housing (710), a cap (720), an ampoule (730), and a carrier (740). Housing (710) is formed of a transparent material (e.g., clear plastic, glass, etc.) and is hollow such that housing (710) insertably receives ampoule (730). Ampoule (730) is also formed of a transparent material (e.g., clear plastic, glass, etc.) and contains a fluid (732). By way of example only, fluid (732) may comprise a liquid growth medium. Such a liquid growth medium is capable of, with incubation, promoting growth of any viable microorganisms it contacts. Fluid (732) also includes a fluorophore whose fluorescence depends on the amount of living microorganisms that may be contained in the liquid medium of fluid (732) after ampoule (730) is fractured as will be described in greater detail below. Fluid (732) is sealed within ampoule (730).

Carrier (740) provides a source of microorganisms or active enzymes. By way of example only, carrier (740) may be impregnated with bacterial spores, other forms of bacteria (e.g., vegetative), and/or active enzymes. By way of example only, spores from *Bacillus, Geobacillus*, and *Clostridium* species may be used. Carrier (740) may be water-absorbent and may be formed of filter material. Sheet-like materials such as cloth, paper, nonwoven polypropylene, rayon or nylon, and microporous polymeric materials may also be used to form carrier (740). Non-water absorbent materials may also be used to form carrier (740), such as metals (e.g., aluminum or stainless steel), glass (e.g., glass beads or glass fibers), porcelain, or plastic. Of course, combinations of the foregoing materials may also be used to form carrier (740).

Ampoule (730) is configured as a frangible component of biological indicator (700), such that ampoule (730) may be fractured within housing to release fluid (732) in housing (710). To assist in the fracture of ampoule (730), a set of fracturing features (750) are disposed in the bottom of housing (710). While fracturing features (750) are shown as spikes in FIG. 4, it should be understood that this is merely illustrative. Fracturing features (750) may take any other suitable form. To further assist in the fracture of ampoule (730), cap (720) is configured to slide downwardly along housing (710) to press ampoule (730) against fracturing features (750). This may be done right before biological indicator (700) is inserted into indicator analyzer (800) as described in greater detail below. It should be understood that ampoule (730) would remain intact while biological indicator (700) is in sterilizing cabinet (150) during a sterilization process. Cap (720) may include one or more openings that allow gasses (e.g., air or sterilant, etc.) to pass into housing (710) before cap (720) is pressed downwardly relative to housing (710) to fracture ampoule (730). These openings may thus enable the microorganisms on carrier (740) to be destroyed by the sterilization process (block 208). However, after cap (720) is pressed downwardly relative to housing (710) to fracture ampoule (730), these one or more openings may be sealed to contain the released fluid (732) in housing (710). When fluid (732) is released from ampoule (730), the released fluid eventually reaches carrier (740), thereby initiating an incubation process with any living microorganisms remaining on carrier (740).

While not shown in FIG. 4, housing (710) may also include an identification tag. Such an identification tag may include a machine readable feature that is capable of being read by identification tag reader (166) of sterilizing cabinet (150) and indicator analyzer (800). By way of example only, the identification tag may comprise an optical code (e.g., a barcode, a data matrix code, a QR code, etc.), an RFID tag, and/or any other suitable kind of machine readable identifier. In addition, the identification tag may include human readable features such as text, numbers, color coding, etc.

Cap (720) may also include a color changing feature. Such a color changing feature may serve as a chemical indicator that changes color when biological indicator (700) is exposed to the sterilant of sterilizing cabinet (150). In some versions, the color changing feature simply changes between two distinctive colors, with one of the colors indicating no exposure to a sterilant and the other color indicating at least some exposure to a sterilant. In some other versions, the color changing feature changes along a range of colors based on the extent to which biological indicator (700) has been exposed to a sterilant. In other words, the color change may be proportional to the degree of sterilant exposure. As yet another merely illustrative example, a color changing feature may change color (e.g., from one of two available colors to another of two available colors; or along a range of colors) in response to a combination of two or more parameters. For instance, such parameters may include (but need not be limited to) time and concentration of sterilant; time, temperature, and concentration or amount/dose of sterilant received; and/or other parameters as will be apparent to those of ordinary skill in the art in view of the teachings herein.

In addition to or in lieu of the foregoing, biological indicator (700) may be configured and operable in accordance with at least some of the teachings of U.S. patent application Ser. No. 15/057,768, entitled "Self-Contained Biological Indicator," filed Mar. 1, 2016, the disclosure of which is incorporated by reference herein. Other suitable forms that biological indicator (700) may take will be described below or will be apparent to those of ordinary skill in the art in view of the teachings herein.

IV. EXEMPLARY BIOLOGICAL INDICATOR ANALYZER

A. Exemplary Biological Indicator Analyzer Hardware

Figure 5:
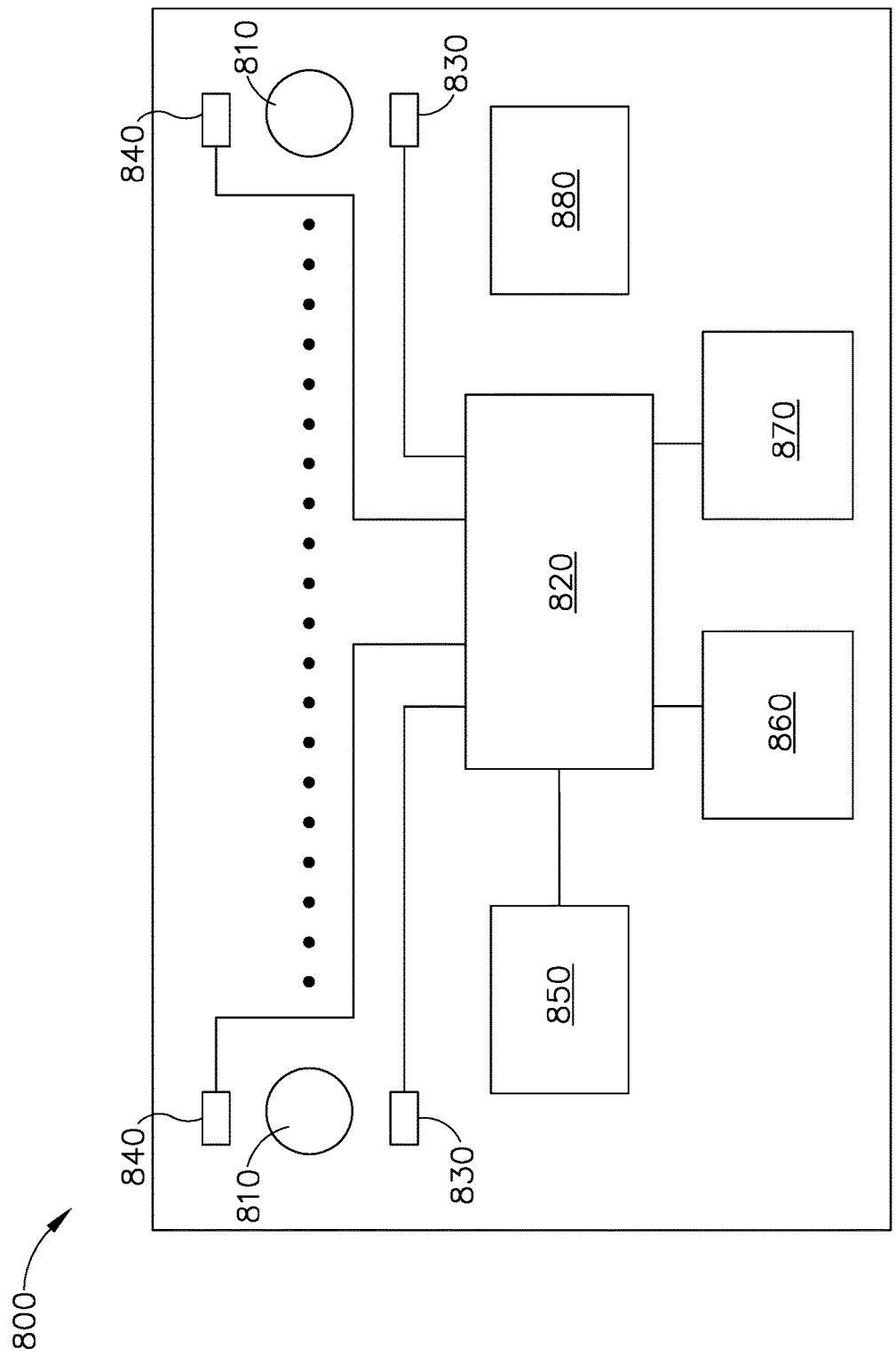
FIG. 5 depicts a schematic view of an exemplary indicator analyzer that may be used to process the biological indicator assembly of FIG. 4 after the biological indicator assembly has undergone a sterilization cycle in the sterilizing cabinet of FIG. 1.

FIG. 5 depicts an exemplary set of components that may be incorporated into biological indicator analyzer (800). In particular, FIG. 5 shows an exemplary biological indicator analyzer (800) that is operable to perform a biological indicator analysis. Biological indicator analyzer (800) of this example comprises a plurality of wells (810), each of which is configured to insertingly receive a respective biological indicator (700). While two wells (810) are shown, it should be understood that any other suitable number of wells (810) may be provided, including eight wells (810), less than eight wells (810), or more than eight wells (810). Biological indicator analyzer (800) also includes a processor (820) that is operable to execute instructions and control algorithms, process information, etc.

Each well (810) has an associated light source (830) and sensor (840). Each light source (830) is configured to project light through housing (710) of the biological indicator (700) that is inserted in the corresponding well (810); and each sensor (840) is operable to detect light fluoresced by fluid (732) contained in housing (710). By way of example only, light source (830) may be in the form of a laser that is configured to emit ultraviolet light. Various other suitable forms that light source (830) may take will be apparent to those of ordinary skill in the art in view of the teachings herein. By way of further example only, sensor (840) may comprise a charge coupled device (CCD). Various other suitable forms that sensor (840) may take will be apparent to those of ordinary skill in the art in view of the teachings herein. As noted above, the fluorescence of fluid (732) will depend on the amount of living microorganisms contained in the medium of fluid (732). Thus, sensor (840) will be able to detect the presence of living microorganisms in fluid (732) based on the degree to which fluid (732) fluoresces in response to light from light source (830).

Biological indicator analyzer (800) of the present example further includes a touch screen display (850). Touch screen display (850) is operable to render various user interface display screens associated with operation of biological indicator analyzer (800). Touch screen display (850) is further configured to receive user input in the form of the user contacting touch screen display (850) in accordance with conventional touch screen technology. In addition, or in the alternative, biological indicator analyzer (800) may include various other kinds of user input features, including but not limited to buttons, keypads, keyboards, a mouse, a trackball, etc. Displays provided through touch screen display (850) may be driven by processor (820). User inputs received through touch screen display (850) may be processed by processor (820).

Biological indicator analyzer (800) of the present example further includes a communication module (860). Communication module (860) is configured to enable bidirectional communication between biological indicator analyzer (800) and a communication hub (not shown), a server, and/or other equipment. In some versions, communication module (860) is configured to communicate with a hub in accordance with at least some of the teachings of U.S. Patent App. No. 62/376,517, entitled "Apparatus and Method to Link Medical Device Sterilization Equipment," filed Aug. 18, 2016, the disclosure of which is incorporated by reference herein. By way of example only, communication module (860) may be configured to provide wired and/or wireless communication via as Ethernet, Wi-Fi, Bluetooth, USB, infrared, NFC, and/or other technologies. Various suitable components and configurations that may be used to form communication module (860) will be apparent to those of ordinary skill in the art in view of the teachings herein. Communications that are sent from or received through communication module (860) are processed through processor (820).

Biological indicator analyzer (800) of the present example further includes an identification tag reader (870), which is operable to read an identification tag of biological indicator (700) as described herein. It should be understood that identification tag reader (870) may be used to identify biological indicator (700) before biological indicator (700) is analyzed. By way of example only, identification tag reader (870) may comprise an optical reader that is operable to read an optical identification tag (e.g., barcode, data matrix code, QR code, etc.) of a biological indicator (700). In addition, or in the alternative, identification tag reader (870) may comprise an RFID reader that is operable to read an RFID identification tag of a biological indicator (700). In some versions where identification tag reader (870) comprises an RFID reader, identification tag reader (870) is also operable to write information to an RFID tag of a biological indicator (700). Various suitable components and configurations that may be used to form identification tag reader (870) will be apparent to those of ordinary skill in the art in view of the teachings herein. Data received through identification tag reader (870) is processed through processor (820).

Biological indicator analyzer (800) of the present example further includes a memory (880), which is operable to store control logic and instructions and that are executed by processor (820) to drive components such as light source (830), touch screen display (850), communication module (860), and identification tag reader (870). Memory (880) may also be used to store results associated with performance of biological indicator analysis, and/or various other kinds of information. Various suitable forms that memory (880) may take, as well as various ways in which memory (880) may be used, will be apparent to those of ordinary skill in the art in view of the teachings herein.

B. Exemplary Biological Indicator Processes and Interfaces

Figure 6:
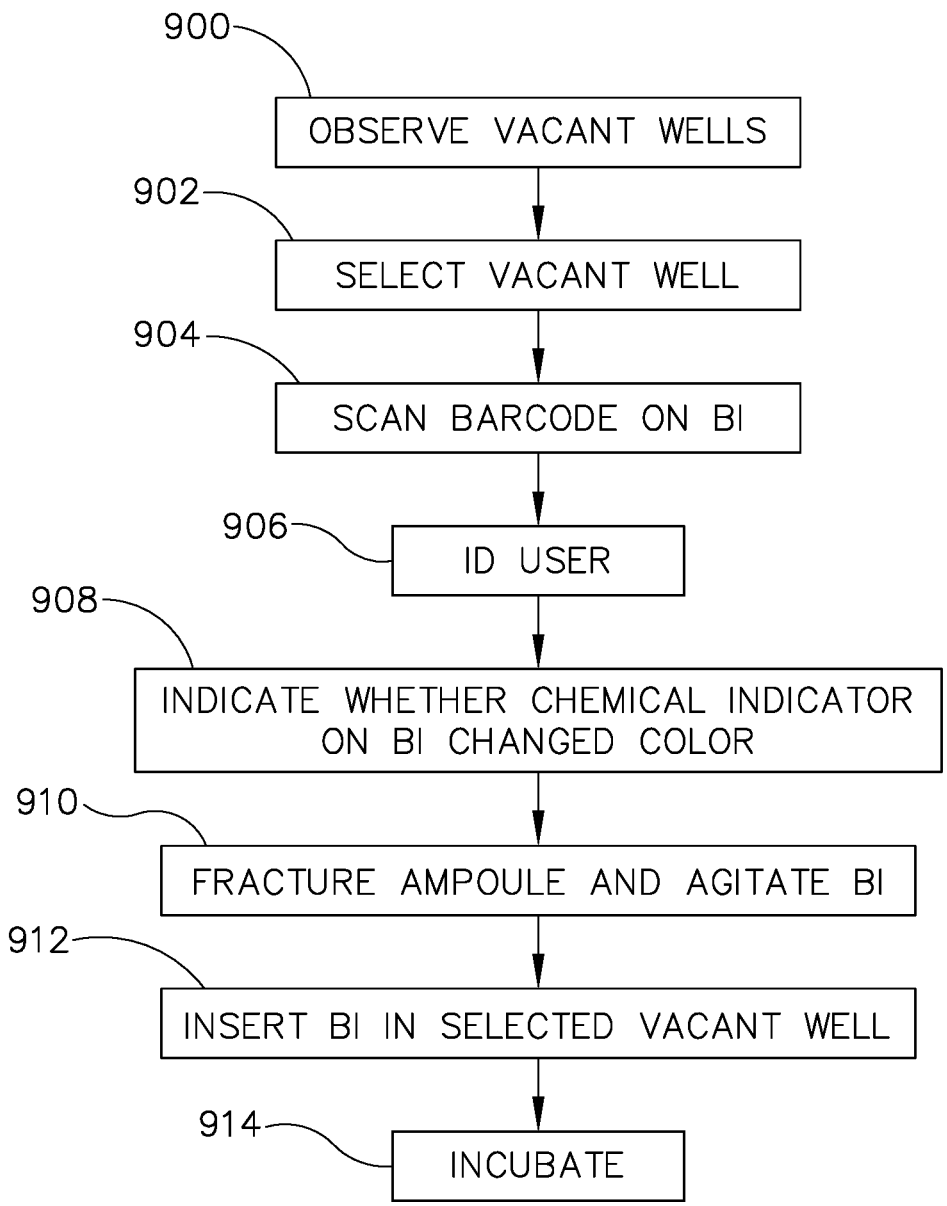
FIG. 6 depicts a flowchart showing an exemplary set of steps that may be performed by a user of the indicator analyzer of FIG. 5 in preparation for analysis of the biological indicator assembly of FIG. 4.

FIG. 6 shows an exemplary set of steps that may be used to initiate biological indicator (700) analysis cycle by biological indicator analyzer (800). As a first step, the user may observe which wells (810) are vacant (block 900) and select a vacant well (block 902). In some versions, touch screen display (850) presents a number next to each vacant well (810), such that the operator simply touches the number associated with the selected vacant well (810) in order to effect selection of that vacant well (block 902). Next, a display screen on touch screen display (850) may prompt the user to place the identification tag of biological indicator (700) near identification tag reader (870) to enable identification tag reader (870) to read the identification tag of biological indicator (700). As part of this prompting, touch screen display (850) may point to the location of identification tag reader (870) to assist the user in finding identification tag reader (870). The user may then use identification tag reader (870) to read the identification tag of biological indicator (700) (block 904).

A display screen on touch screen display (850) may then prompt the user to identify himself or herself. The user may then manipulate touch screen display (850) to identify himself or herself (block 906). A display screen on touch screen display (850) may then prompt the user to indicate whether the chemical indicator on cap (720) of biological indicator (700) has changed color. The user may then manipulate touch screen display (850) to indicate whether the chemical indicator on cap (720) of biological indicator (700) has changed color (block 908).

A display screen on touch screen display (850) may then prompt the user to prepare biological indicator (700) for loading into the selected well (810) by fracturing ampoule (730) and agitating biological indicator (700). The operator may then fracture ampoule (730) by pressing on cap (720), then agitate biological indicator (700) (block 910) to ensure proper mixing of fluid (732) with carrier (740). The user may then quickly place biological indicator (700) in the selected well (810) (block 912). In some instances, it may be desirable to insert biological indicator (700) in the selected well (810) (block 912) immediately after fracturing ampoule (730) and agitating biological indicator (700) (block 910).

In some versions, indicator analyzer (800) is configured to determine whether the user appropriately completed the step of fracturing ampoule (730) and agitating biological indicator (700) (block 910) before inserting biological indicator (700) in the selected well (810) (block 912). By way of example only, this may be determined based on how sensor (840) detects light emitted by light source (830) after biological indicator (700) is inserted in the selected well (810). In the event that indicator analyzer (800) determines that the user failed to appropriately complete the step of fracturing ampoule (730) and agitating biological indicator (700) (block 910) before inserting biological indicator (700) in the selected well (810) (block 912), touch screen display (850) may prompt the user to withdraw biological indicator (700) from well (810) and properly complete the step of fracturing ampoule (730) and agitating biological indicator (700) (block 910).

To the extent that the user has properly completed the step of fracturing ampoule (730) and agitating biological indicator (700) (block 910), and then inserted biological indicator (700) in the selected well (block 912), biological indicator (700) is allowed to sit in well (810) for an incubation period (block 914). During the incubation period (block 914), light source (830) associated with the selected well (810) is activated and sensor (840) monitors responsive fluorescence of fluid (732) in indicator (700). Well (810) may also be heated (e.g., to approximately 60° C.) during the incubation period (block 914). As noted above, fluid (732) includes a fluorophore whose fluorescence depends on the amount of microorganisms contained in the medium. Thus, sensor (840) can detect the presence of living microorganisms (from carrier (740)) in fluid (732) based on the fluorescence of fluid (732). It should therefore be understood that, after a suitable incubation period has passed, indicator analyzer (800) will conclude whether any of the microorganisms that were on carrier (740) (i.e., before the sterilization cycle in sterilization cabinet (150)) survived the sterilization cycle in sterilization cabinet (150), based on the fluorescence of fluid (732) as sensed by sensor (840).

By way of example only, the incubation period (block 914) may be approximately 30 minutes. Alternatively, the incubation period may be substantially longer (e.g., one or more hours), shorter, or of any other suitable duration. During the incubation period (block 914), touch screen display (850) may provide a graphical representation of the amount of time remaining in the incubation period. When more than one well (810) is occupied by a corresponding biological indicator (700), touch screen display (850) may provide a graphical representation of the amount of time remaining in the incubation period for each occupied well (810). In addition to the foregoing, indicator analyzer (800) may be configured and operable in accordance with at least some of the teachings of U.S. Provisional Patent App. No. 62/316,722, the disclosure of which is incorporated by reference herein.

V. EXEMPLARY VARIABLE RESISTANCE BIOLOGICAL INDICATOR

As noted above, a biological indicator (700) may have openings in cap (720), housing (710), or elsewhere that will allow gasses (e.g., air or sterilant, etc.) to pass into housing (710) and expose the microorganisms contained therein to sterilant. The size and/or configuration of such an opening can be chosen during manufacture to allow for a desired level of resistance to gasses or other substances entering biological indicator (700), with smaller openings providing a lower volume of flow and resulting in a higher resistance, and larger openings providing a higher volume of flow and resulting in a lower resistance. Different sterilization cycles that may use a biological indicator (700) may operate at varying levels of pressurization, varying durations, and may use varying types of sterilant in order to achieve proper sterilization of the numbers and types of medical devices being sterilized.

Due to the variety of factors that must be accounted for in the interactions between a particular sterilization cycle and a biological indicator (700), in some instances a biological indicator (700) with a particular vent size or configuration chosen at the time of manufacture may not be ideal for the sterilization cycle it is used with. For example, certain sterilization cycles may operate at a high pressure in order to ensure sterilization of instruments that have movable joints, long and narrow lumens, or other features that might be difficult to reach with sterilant. However, a biological indicator (700) with a particular vent size or configuration and corresponding resistance chosen at the time of manufacture may not offer a level of resistance that ideally simulates the hard to reach areas of the above instrument. In order to address the circumstances where a standard static resistance biological indicator (700) may not be ideally suited for the chosen sterilization cycle, a variable resistance biological indicator (1200) and variable resistance biological indicator cap (1230) are described herein, which can support multiple openings sizes or configurations, and thereby selectively provide multiple corresponding resistances, such that a level of resistance may be selected at the time of use rather than at the time of manufacture.

A. Exemplary Variable Resistance Biological Indicator with Body Display

Figure 7A:
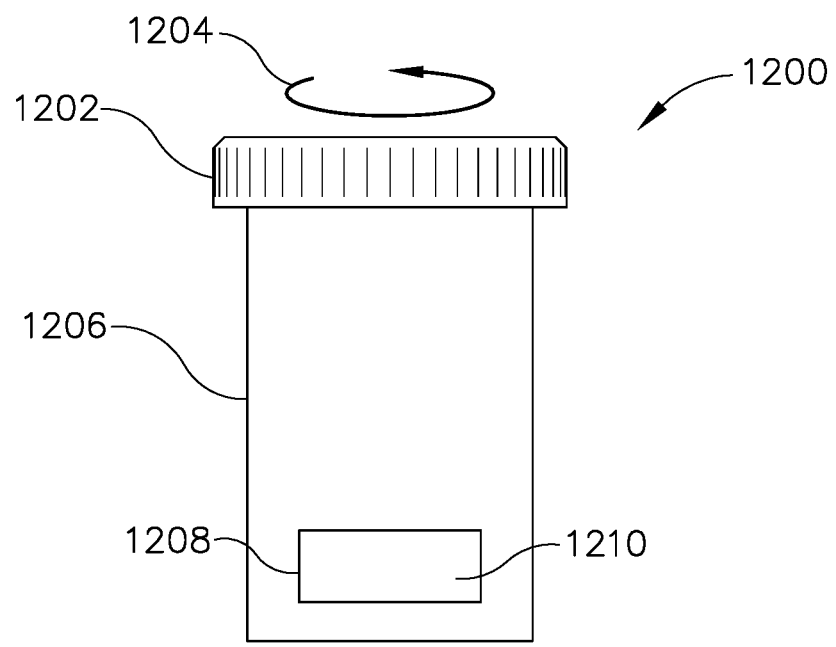
FIG. 7A depicts a side elevational view of an exemplary alternative biological indicator assembly of FIG. 4 that may be used to perform any of the methods of FIGS. 9-13, with the biological indicator assembly in a first state.
Figure 7B:
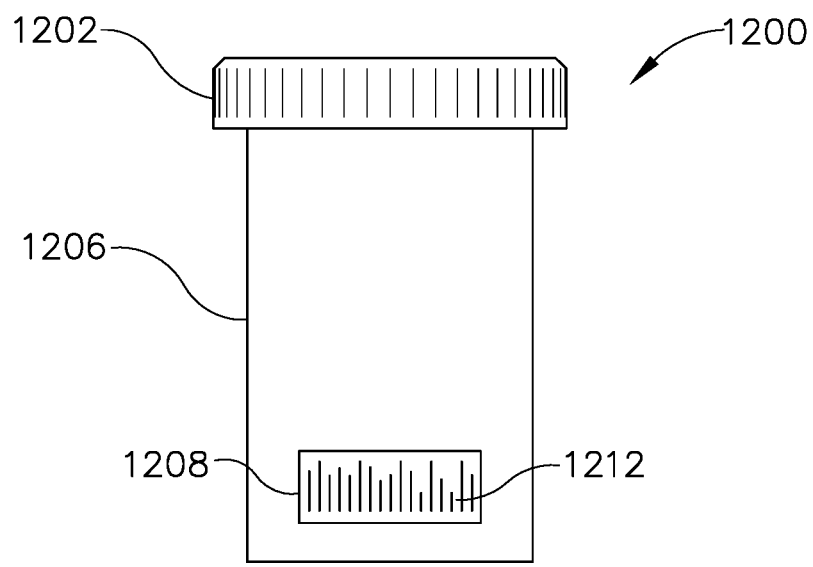
FIG. 7B depicts a side elevational view of the biological indicator assembly of FIG. 7A, with the biological indicator assembly in a second state.

FIGS. 7A and 7B show an exemplary biological indicator (1200) with a body displayed resistance indicator (1212). Except as otherwise described below, biological indicator (1200) of this example may have the same components and functionality as biological indicator (700) described above. For instance, biological indicator (1200) of this example has a housing (1206), a cap (1202), openings in cap (1202) to allow sterilant to enter, and other internal components not pictured in FIGS. 7A-7B.

The variable biological indicator (1200) of this example also includes an inner housing (1210) that is able to rotate separately from the outer housing (1206). Portions of inner housing (1210) are visible through an indicator viewer or window (1208) in outer housing (1206). The variable resistance biological indicator (1200) additionally has a rotatable cap (1202) that is configured to rotate relative to outer housing (1206) when a rotational force (1204) is applied. Rotatable cap (1202) is secured to inner housing (1210) such that rotation of the rotatable cap (1202) relative to outer housing (1206) will cause the inner housing (1210) to rotate relative to outer housing (1206). In effect, this allows differing portions of inner housing (1210) to be displayed through the window (1208) as rotatable cap (1202) is rotated, causing the inner housing (1210) to rotate inside the outer housing (1206).

In the present example, rotation of the rotatable cap (1202) and the inner housing (1210) also causes openings or vents (not pictured) in the cap (1202) to change in effective size, thereby providing variable venting configurations. By providing variable venting configurations, biological indicator (1200) will vary the resistance provided to the sterilant of sterilizing cabinet (150) reaching the microorganisms contained within biological indicator (1200). In other words, with cap (1202) providing a first venting configuration, the sterilant of sterilizing cabinet (150) may encounter a first degree of resistance in reaching the microorganisms contained within biological indicator (1200). With cap (1202) providing a second venting configuration, the sterilant of sterilizing cabinet (150) may encounter a second degree of resistance in reaching the microorganisms contained within biological indicator (1200). It should be understood that cap (1202) may be operable to selectively provide any suitable number of different venting configurations.

By way of example only, different venting configurations may be provided by having vents of different sizes placed around the circumference of cap (1202) and housing (1206), so that when cap (1202) is at a first rotational position relative to housing (1206), a small vent in cap (1202) lines up with a small vent in housing (1206) while other vents are blocked, limiting the effective size of the vents to the size of the opened small vent. As cap (1202) is rotated to a second position relative to outer housing (1206), a medium sized vent or, for example, two small vents, line up with a similar size and number of vents in housing (1206), while other vents are blocked, limiting the effective size of the vents to the medium vent or the two small vents. In this manner, as the cap (1202) is rotated relative to the outer housing (1206), the effective size of vents can be adjusted, allowing sterilant to encounter varying levels of resistance in order to enter the housing (1210).

In addition to allowing a rotational force (1204) to rotate the cap (1202) to one or more positions to allow a variable level of resistance, rotation of the cap (1202) may also simultaneously expose one or more resistance indicators (1212). While some portions of the inner housing (1210) may be blank or may by color, text, or other visual identifier indicate a neutral state, other portions of inner housing (1210) may have one or more resistance indicators (1212) that may be exposed through the window (1208) of the outer housing (1206) as cap (1202) is rotated. It should be understood that, since rotation of cap (1202) relative to outer housing (1206) will simultaneously change the venting configuration and the exposure of a particular resistance indicator (1212) through window (1208), the particular resistance indicator (1212) that is exposed through window (1208) will be indicative of the particular venting configuration provided by cap (1202).

Each resistance indicator (1212) may comprise one or more human readable indicators, machine readable indicators, or both. Human readable indicators may include, for example, numbers, letters, text, symbols, colors, patterns, or other indicators which may be readily perceived by a user. Machine readable indicators may include, for example, any human readable indicator that may be readily captured and interpreted by a machine, imaging device, or computer, as well as barcodes, data matrix codes, QR codes, other visually encoded data, data containing RFID chips, data containing NFC chips, other wirelessly transmitted data, or similar technologies. In the case of passive tags such as RFID chips, NFC chips, or other indicators that may transmit data wirelessly, outer housing (1206) may additionally contain an electromagnetic shielding such as a layer of aluminum or another appropriate material that may prevent a wireless scanning device from detecting machine readable indicators that are covered by the outer housing (1206), while allowing a single machine readable indicator (1212) that is exposed through the window (1208) to be successfully read by the scanning device.

In an example such as that shown in FIG. 7B, a human readable portion of a resistance indicator (1212) may assist a user in rotating the cap (1202) to an appropriate position given such factors as the sterilization cycle type that the biological indicator is being used in, the type of sterilizing cabinet (150) being used, or other factors. The machine readable portion of the resistance indicator (1212) may allow an imaging device, such as a barcode scanner, or a wireless device, such as an RFID reader, to capture data from the machine readable portion and verify it against other records to, for example, ensure that an appropriate level of resistance has been configured by the user for that sterilization cycle type or sterilizing cabinet (150) type.

The number of different vent configurations and corresponding indicators (1212) may vary by implementation, and it should be understood that cap (1202) and outer housing (1206) may be configured to provide any suitable number of vent configurations to choose from. Likewise, the size of the window (1208) and the indicator (1212) may be varied greatly to suit almost any needed number of resistance indicators (1212). For example, in versions where a sterilizing cabinet (150) may support four different types of sterilizing cycles, each having their own optimal level of biological indicator resistance, cap (1202) and outer housing (1206) may be operable to provide five different venting configurations. These different venting configurations could include a sealed or non-vented configuration for use when biological indicator (1200) is in storage; a first vented configuration corresponding to a first sterilization cycle; a second vented configuration corresponding to a second sterilization cycle; and so on. Each of the first, second, third, and fourth vented configurations could result in an effective vent size appropriate for the corresponding sterilization cycle; and also cause the window (1208) to display a human readable indicator (1212) identifying the corresponding sterilization cycle type, a machine readable indicator (1212) identifying the corresponding sterilization cycle type, or both.

Some machine readable resistance indicators (1212), such as RFID and NFC chips, may also allow a scanning device to write data to the RFID or NFC chip that may then remain associated with that biological indicator (1200), providing an additional useful way to associate data with a biological indicator (1200) on an ad hoc basis. These additional capabilities allow a system to be implemented to automatically verify user configurations of biological indicators (1200) in order to reduce human error; and also create additional sources of data that may be used to, for example, allow offline operation of the system or provide further automated safeguards against human error. Such implementations include those discussed in further detail below and others that will be apparent to one of ordinary skill in the art in light of the disclosure herein.

While the variable resistance biological indicator (1200) of FIGS. 7A-7B has been described as using a rotational movement of a cap (1202) or housing (1206) to allow adjustment to one or more different venting configurations while also revealing corresponding human and/or machine readable indicators (1212), it should be understood that other types of adjustment are possible as will be apparent to one of ordinary skill in the art in light of the disclosure herein. For example, a sliding portion of housing (1206) could be moved linearly along a track or slot in order to expose or reveal vents and indicators, a removable pull tab could be removed in order to expose or reveal vents and indicators, or other features may be used to provide variable venting configurations.

B. Exemplary Variable Resistance Biological Indicator with Cap Display

Figure 8A:
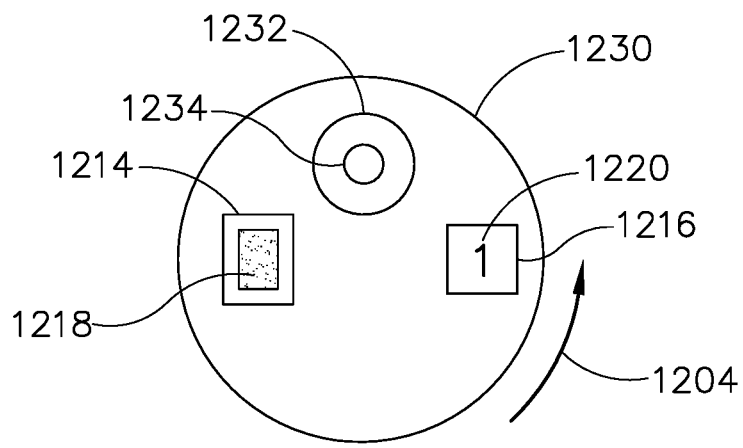
FIG. 8A depicts a top plan view of another exemplary alternative biological indicator assembly of FIG. 4 that may be used to perform any of the methods of FIGS. 9-13, with the biological indicator assembly in a first state.
Figure 8B:
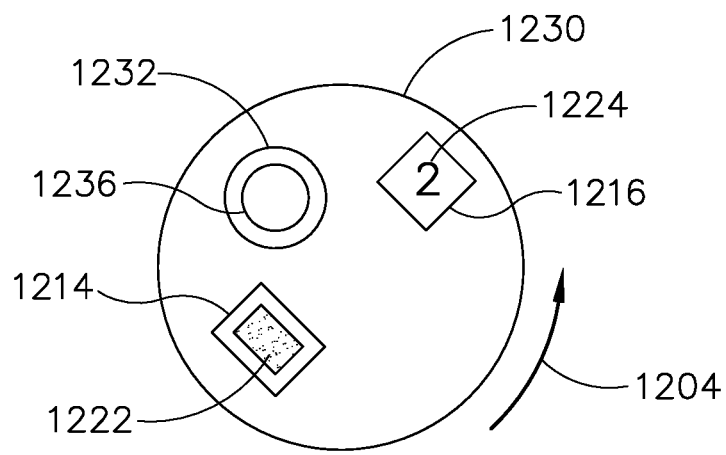
FIG. 8B depicts a top plan view of the biological indicator assembly of FIG. 8A, with the biological indicator assembly in a second state.
Figure 8C:
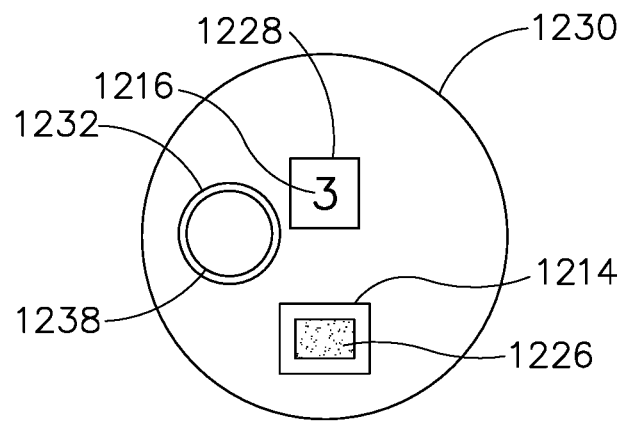
FIG. 8C depicts a top plan view of the biological indicator assembly of FIG. 8A, with the biological indicator assembly in a third state.

FIGS. 8A-8C show an exemplary variable resistance biological indicator cap (1230) with a cap displayed resistance indicator (1218, 1222, 1226). The variable resistance biological indicator cap (1230) of FIGS. 8A-8C may be used with a variety of biological indicators such as the biological indicator (700) of FIG. 4, the biological indicator (1200) of FIGS. 7A-7B, or other biological indicators. The variable resistance biological indicator cap (1230) of FIGS. 8A-8C may also have variable openings or vents (1232, 1234, 1236, 1238) to allow sterilant to reach the microorganisms contained within biological indicator (700, 1200) with a selected degree of resistance during a sterilization cycle.

As shown in FIG. 8A, the variable resistance biological indicator cap (1230) of the present example has a machine readable indicator window (1214), a human readable indicator window (1216), and a primary vent (1232) passing through an outer surface of the variable resistance biological indicator cap (1230). The variable resistance biological indicator cap (1230) of the present example also has an inner surface (not pictured) with human readable indicators (1220, 1224, 1228) printed or affixed to the inner surface, machine readable indicators (1218, 1222, 1226) printed or affixed to the inner surface, and varying sizes of control vents (1234, 1236, 1238) passing through the inner surface. The inner surface may be a disc or other shape sized to fit within the variable resistance biological indicator cap (1230). The inner surface may be fixed or connected to the housing (710, 1206) of a biological indicator (700, 1200) such that the inner surface is rotationally fixed relative to the housing (710, 1206). The outer surface of the variable resistance biological indicator cap (1230) is movably coupled with the inner surface on a track, rail, or other mount such that it may rotate independently of the inner surface when a rotational force (1204) is applied to the variable resistance biological indicator cap (1230), thereby causing the outer surface to rotate relative to the housing (710, 1206) while the inner surface remains stationary relative to the housing (710, 1206).

As the outer surface of the variable resistance biological indicator cap (1230) rotates relative to the stationary inner surface, the indicator windows (1214, 1216) will rotate over top of the stationary inner surface and expose one or more human readable indicators (1220, 1224, 1228), machine readable indicators (1218, 1222, 1226), or both depending upon the position that the outer surface of the variable resistance biological indicator cap (1230) is rotated to. Simultaneously, as the variable resistance biological indicator cap (1230) rotates, the primary vent (1232) will be positioned over top of a particular control vent (1234, 1236, 1238). Thus, the variable resistance biological indicator cap (1230) will simultaneously change the venting configuration to an effective vent size matching the size of a control vent (1234, 1236, 1238), change the exposure of a corresponding human readable indicator (1220, 1224, 1228), and change the exposure of a corresponding machine readable indicators (1218, 1222, 1226) when the variable resistance biological indicator cap (1230) is rotated relative to the outer housing (710, 1206) of biological indicator (700, 1200).

FIG. 8A shows the variable resistance biological indicator cap (1230) rotated to a first position that exposes a first human readable indicator (1220) and a first machine readable indicator (1218), while primary vent (1232) is positioned over top of a first control vent (1234), resulting in an effective vent size matching the first control vent (1234). FIG. 8B shows the variable resistance biological indicator cap (1230) rotated to a second position that exposes a second set of indicators (1222, 1224), while primary vent (1232) is positioned over top of a second control vent (1236), resulting in an effective vent size matching the second control vent (1236). As shown, second control vent (1236) is larger than first control vent (1234), such that first control vent (1234) provides greater resistance to sterilant than second control vent (1236). FIG. 8C shows the variable resistance biological indicator cap (1230) rotated to a third position that exposes a third set of indicators (1226, 1228), while primary vent (1232) is positioned over top of a third control vent (1238), resulting in an effective vent size matching the third control vent (1238). As shown, third control vent (1238) is larger than second control vent (1236), such that second control vent (1236) provides greater resistance to sterilant than third control vent (1238). While FIG. 8A-8C show one possible arrangement of the control vents (1234, 1236, 1238), human readable indicators (1220, 1224, 1228), and machine readable indicators (1218, 1222, 1226), other arrangements will be apparent to those of ordinary skill in the art in light of the disclosure herein.

As with the body display indicator of FIGS. 7A and 7B, the human readable portion of a resistance indicator (1220, 1224, 1228) may assist a user in rotating the variable resistance biological indicator cap (1230) to an appropriate position to achieve a desired venting configuration, given such factors as the sterilization cycle type that the biological indicator (700, 1200) is being used in, the type of sterilizing cabinet (150) being used, or other factors. The machine readable portion of the resistance indicator (1218, 1222, 1226) may allow an imaging device, such as identification tag reader (166), or a wireless device, such as an RFID reader, to capture data from the machine readable portion and verify it against other records to, for example, ensure that an appropriate level of resistance has been configured by the user for that sterilization cycle type or cabinet (150) type.

In versions where the machine readable portion comprises an RFID feature, an NFC feature, or similar feature, variable resistance biological indicator cap (1230) may also have a layer of electromagnetic shielding material between the outer surface and the inner surface in order to prevent an RFID or NFC scanning device from reading information from machine readable indicators (1218, 1222, 1226) that are not exposed through the machine readable indicator window based upon the current position of the variable resistance biological indicator cap (1230). The number of positions supported by the variable resistance biological indicator cap (1230) may vary, but it should be understood that the size and arrangement of indicators (1218, 1220, 1222, 1224, 1226, 1228), indicator windows (1214, 1216), and vents (1232, 1234, 1236, 1238) can be varied to support almost any needed number of positions corresponding to venting configurations.

It should also be noted that, while FIGS. 8A-8C show a variable resistance biological indicator cap (1230) that is adjusted by rotation of an outer surface of the variable resistance biological indicator cap (1230) relative to an inner surface, a similar adjustment could also be achieved with an outer surface portion that slides in one or more directions along a track, rail, or other mount relative to an inner surface rather than rotating, with different positions along the track corresponding to different venting configurations as described above, or with removable pull tabs that can be removed from the outer surface to reveal one or more corresponding indicators (1218, 1220, 1222, 1224, 1226, 1228) and control vents (1234, 1236, 1238).

As with the biological indicator (1200) of FIGS. 7A and 7B, some machine readable resistance indicators (1212), such as RFID and NFC chips, may also allow a scanning device to write data to the RFID or NFC chip that may then remain associated with that biological indicator (700, 1200), providing an additional useful way to associate data with a biological indicator (700, 1200) on an ad hoc basis. These additional capabilities allow a system to be implemented to automatically verify user configurations of biological indicators (700, 1200) in order to reduce human error, and also create additional sources of data that may be used to, for example, allow offline operation of the system or provide further automated safeguards against human error. Such implementations include those discussed in further detail below and others that will be apparent to one of ordinary skill in the art in light of the disclosure herein.

VI. EXEMPLARY METHODS OF USING VARIABLE RESISTANCE BIOLOGICAL INDICATORS

The variable resistance biological indicators (700, 1200) disclosed above offer several advantages in addition to the ability to adjust resistance of exposure of microorganisms to sterilant from sterilizing cabinet (150). For example, since machine readable indicators (1212, 1218, 1222, 1226) can be exposed or hidden as part of the same adjustment that changes resistance for a biological indicator (700, 1200) (e.g. a cap (1202) or variable resistance biological indicator cap (1230) rotation that adjusts vent size while also exposing an indicator (1212, 1218, 1222, 1226) on the housing (1206) or the variable resistance biological indicator cap (1230)) the current configuration of any given biological indicator (700, 1200) can be automatically determined based upon the machine readable indicator (1212, 1218, 1222, 1226) that is currently exposed at any point of contact that the biological indicator (700, 1200) has with a device having an appropriate scanner. This could include a sterilizing cabinet (150) visually scanning a visual indicator or electromagnetically scanning an RFID or NFC indicator via a visual scanner or RFID transceiver placed near or within the sterilizing cabinet (150), or, for example, via identification tag reader (166) having such capabilities. This could also include using a similar scanner or identification tag reader (870) at an indicator analyzer (800), a handheld scanner, mobile phone, or other mobile device that could be used for identifying biological indicators as they change hands or are disposed of after use, or other devices that may come into contact with a variable resistance biological indicator (1200).

Each point of contact where a biological indicator (700, 1200) is scanned provides an opportunity to read information from a machine readable indicator (1212, 1218, 1222, 1226), which could include a current variable resistance vent configuration, but could also include a unique identifier for that biological indicator (700, 1200). In such versions, a biological indicator (700, 1200) could generate a trail of unique identifications as it moved from receipt, to storage, to use in a sterilization cycle, to incubation and analysis, then to disposal, with each unique identification point being stored in a record server. With such a data set available, any biological indicator (700, 1200) can be related back to the sterilization cycles and procedures it was used in, and any sterilization cycle or procedure may be related back to a biological indicator (700, 1200) that it is associated with. This provides numerous opportunities to both identify and reduce human error such as when a biological indicator (700, 1200) is used in a sterilization cycle and then misplaced or misidentified due to human error, when a biological indicator (700, 1200) is used in a sterilization cycle and then mistakenly left in the sterilizing cabinet (150), or other scenarios in which a detailed history available from the record server may aid to reconstruct events. Additionally, in versions having machine readable indicators that include some form of memory, such as an RFID or NFC indicator, there is an additional capability to write some or all of the audit trail data to the biological indicator (700, 1200) itself. This could allow for continued retention of data, transmission of data between devices, and reconstruction of past events even when network communications are interrupted or the record server is unavailable for any reason, or when a sterilizing cabinet (150) is not directly networked with an indicator analyzer (800), for example.

The following discussion provides various examples of how biological indicators (700, 1200) with variable resistance features may be used in a system formed by a sterilizing cabinet (150), a biological indicator analyzer (800), and other components. Other suitable ways in which biological indicators (700, 1200) with variable resistance vent features may be used in such systems will be apparent to those of ordinary skill in the art in view of the teachings herein.

A. Exemplary Basic Steps for Using Variable Resistance Indicator

As disclosed above, a variable resistance biological indicator (700, 1200) may provide a number of features or advantages beyond the ability to adjust the resistance of a cap vent or other opening to control the flow of sterilant into the biological indicator (700, 1200). While taking advantages of different features may require particular system components, network configurations, or methods of use, some basic steps may be shared by many implementations and methods. For example, while FIGS. 7-11 show different exemplary methods of using a variable resistance biological indicator (700, 1200) with some or all of the features described above, each of the shown exemplary methods has a common set of initial steps. However, while these common steps are shared by FIGS. 7-11, it should not be assumed that any method of using a variable resistance biological indicator (700, 1200) must begin with these steps.

Figure 9:
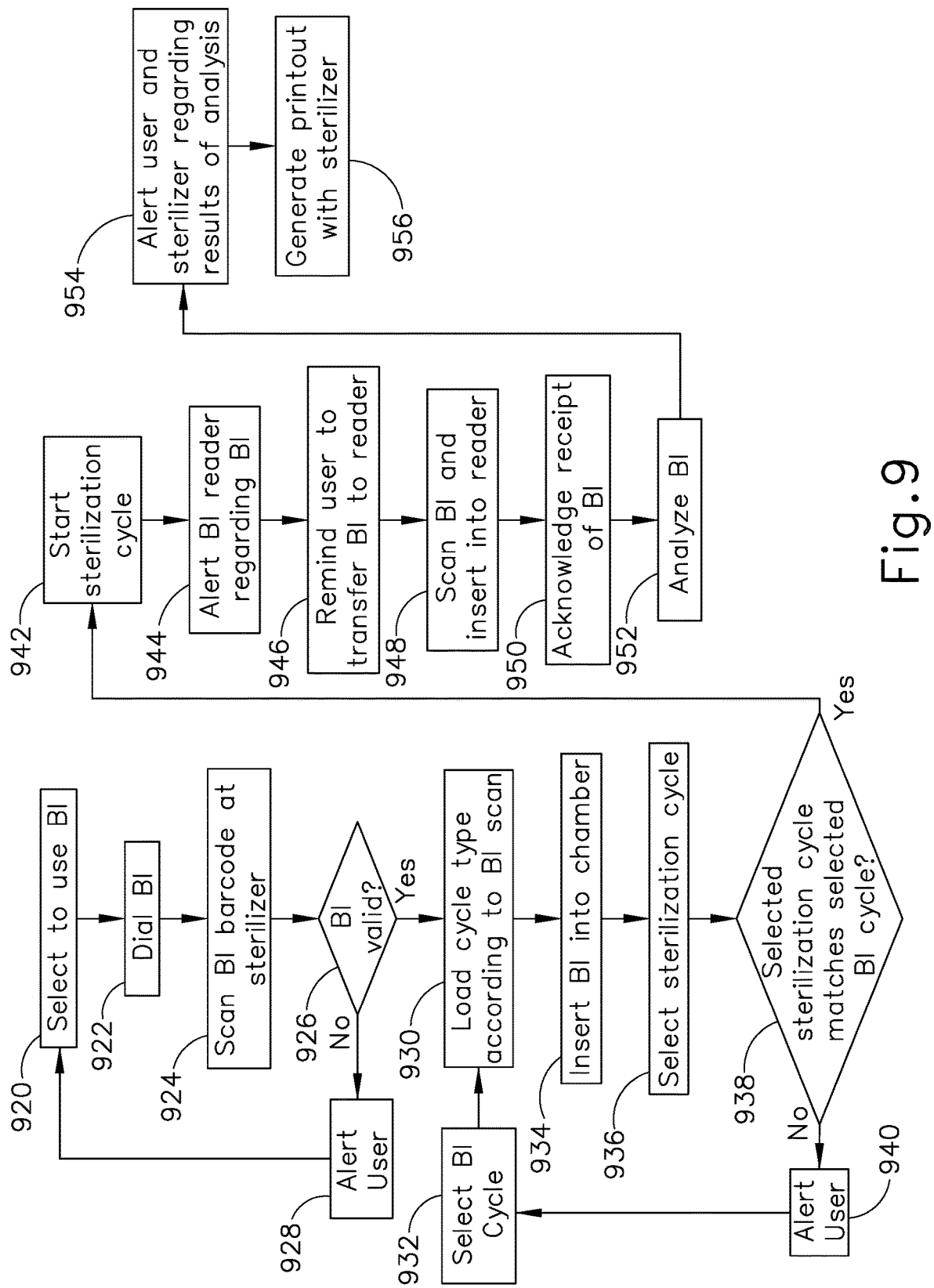
FIG. 9 depicts a flowchart showing an exemplary set of steps that may be performed using a modified version of the sterilizing cabinet of FIG. 1, using a modified version of the indicator analyzer of FIG. 5, and using a modified version of the biological indicator assembly of FIG. 4.

FIG. 9 shows a set of steps that may be performed with a variable resistance biological indicator (700, 1200), sterilizing cabinet (150), and indicator analyzer (800) in order to determine the efficacy of a sterilization cycle while reducing the potential for human error associated with the use of the variable resistance biological indicator (700, 1200). Initially, a user may select (block 920) or make an indication that they would like to perform a sterilizing cycle with a biological indicator (700, 1200) via touch screen display (160) (or some other interface) of the sterilizing cabinet (150). A user may also select (block 922) the vent configuration to provide a desired level of variable resistance for a variable resistance biological indicator (700, 1200) by rotating the cap (1202), variable resistance biological indicator cap (1230), or body (1206) so that the opening or window (1208, 1214, 1216) shows a human readable indicator (1212, 1220, 1224, 1228) and/or machine readable indicator (1212, 1218, 1222, 1226) that correspond to the appropriate sterilizing cycle that has been or will be selected via the sterilizing cabinet (150). It should be understood that touch screen display (160) (or some other interface) of the sterilizing cabinet (150) may prompt the user what vent configuration to select based on the user's sterilization cycle selection, based on load characteristics (e.g., materials, geometries, quantities, temperature, etc.), and/or based on other factors.

As described above in relation to the variable resistance biological indicator with body display (1200) and variable resistance biological indicator cap (1230) with cap display, rotating or otherwise positioning the cap (1202) or the variable resistance biological indicator cap (1230) at a position where one or more indicators (1212, 1218, 1220, 1222, 1224, 1226, 1228) are shown, based on the selection step (block 922), also places the variable resistance biological indicator (1200) or variable resistance biological indicator cap (1230) in a venting configuration that corresponds to the shown indicators (i.e. by aligning a primary vent (1232) over top of a control vent (1234, 1236, 1238) or a similar implementation). The user may also scan or otherwise read (block 924) one or more machine readable indicators (1212, 1218, 1222, 1226) from the variable resistance biological indicator (700, 1200) using identification tag reader (166), some other barcode scanner, an RFID scanner, or some other appropriate scanner.

Information retrieved by scanning (block 924) may include, for example, an indication of the current level of variable resistance provided by the selected vent configuration, the sterilization cycle that the selected level of variable resistance is associated with, a biological indicator (700, 1200) identifier, a biological indicator (700, 1200) batch identifier, a biological indicator (700, 1200) manufacturer identifier, a biological indicator (700, 1200) expiration date, and/or other information that may readily be encoded within a barcode or other image, or an RFID chip or other short range wireless device. Such information may be used to determine if the biological indicator (700, 1200) selected by the user is valid (block 926), or whether, for example, an unsupported vent configuration has been chosen, the biological indicator (700, 1200) has expired, the biological indicator (700, 1200) is not supported for that sterilizing cabinet (150) or selected sterilization cycle, the biological indicator (700, 1200) has already been used in a different sterilization cycle, that batch of biological indicators (700, 1200) has been flagged or recalled by the manufacturer, or other similar reasons for invalidity. If any information provided by the scan (block 924) indicates that the biological indicator is erroneously configured (i.e. by having been rotated to an improper position) or otherwise unusable, the sterilizing cabinet (150) may alert (block 928) the user of one or more problems that may need to be addressed before the sterilization cycle begins.

If it is determined that the biological indicator (700, 1200) is validly configured and usable (block 926), the sterilizing cabinet (150) may unlock or open the sterilizing chamber (152), if it is locked, or otherwise allow a user to load (block 930) the medical devices or other instruments that are to be sterilized in sterilizing chamber (152); and place (block 934) the selected biological indicator (700, 1200) in sterilizing chamber (152). The sterilizing cabinet (150) may also prompt or allow the user to select or confirm (block 936) the sterilization cycle that is to be performed. The sterilizing cabinet (150) may then confirm that the selected (block 936) sterilization cycle matches the sterilization cycle that the variable resistance biological indicator (700, 1200) was configured for (block 922) based upon the data scanned (block 924) from the variable resistance biological indicator (700, 1200). If it is determined that the sterilization cycle selected (block 936) via the sterilizing cabinet (150) does not match the sterilization cycle or variable resistance that the biological indicator (700, 1200) was configured for (block 922), the user may be alerted (block 940) indicating the mismatch and given a chance to select (block 932) a new cycle via the sterilizing cabinet (150) or select (block 932) a new vent configuration for the biological indicator (700, 1200) by removing it from the sterilizing cabinet (150) and rotating the cap (1202), variable resistance biological indicator cap (1230), or housing (1206).

Many of the of the initial steps discussed above may, in some versions, be enforced by automated means, such as locking the sterilizing cabinet (150) sterilizing chamber (152) until the biological indicator (700, 1200) is scanned (block 924), unlocking and opening the door to sterilizing chamber (152) when a cycle mismatch is detected (block 938), creating audible alerts when an error is detected (block 928, block 940), using a scanner within the sterilizing chamber (152) to re-scan the biological indicator (700, 1200) after it has been placed and after the sterilizing chamber (152) has been sealed to ensure that biological indicator (700, 1200) has not been reconfigured since the first scan (block 924), or other safeguards. Many of the initial steps may also be shown or explained to a user of the sterilizing cabinet (150) via a touch screen display (160) or other display, and may include, for example, pictures and text showing or explaining proper variable resistance biological indicator (700, 1200) rotation and configuration, scanning, load placement, biological indicator (700, 1200) placement, and other helpful information.

After one or more of these exemplary initial steps are performed, a set of variable steps may be performed to complete the process, with the variable steps being determined based upon such factors as network capabilities, system components and capabilities, or other factors, as described below or as will be apparent to those of ordinary skill in the art in light of the disclosure herein.

B. Exemplary Cycle Completion with Scanner and Network with Sterilizing Cabinet as Master Device The remaining exemplary steps of FIG. 9, beginning after a successful determination (block 938) that a sterilization cycle selected via the sterilizing cabinet (150) matches a vent configuration selected on the variable resistance biological indicator (700, 1200), may be appropriate for a system that uses a visual scanner or wireless scanner for scanning (block 924) identifiers of biological indicators (700, 1200) and which has a stable network that will allow network communication between the sterilizing cabinet (150) and the indicator analyzer (800). The exemplary steps of FIG. 9 may also show a preference for treating the sterilizing cabinet (150) as the master device, which may be appropriate where the sterilizing cabinet (150) has a dedicated user or clinician, or where an indicator analyzer (800) has limited ability to output information or interact with a user.

The sterilizing cabinet (150), having been unable to identify any erroneous configurations or other problems, may start the sterilization cycle (block 942), which may include load conditioning, injection of sterilization, pressure adjustments, and other actions as discussed above with reference to FIGS. 2-3. The sterilizing cabinet (150) may also alert (block 944) the indicator analyzer (800) via the network that a sterilization cycle is currently being performed using a biological indicator (700, 1200), so that information is available via the indicator analyzer (800) identifying the sterilization cycle type, sterilizing cabinet (150), biological indicator (700, 1200) identifier, time, date, and other information relating to the sterilizing cycle that may be pertinent to the biological indicator (700, 1200) analysis. Such information could be used to assist a user of the indicator analyzer (800) in prioritizing use of the indicator analyzer (800) or other tasks that may need to be completed before the new biological indicator (700, 1200) arrives for analysis.

When the sterilization cycle completes, the sterilizing cabinet (150) may remind (block 946) a user via a display (160) or other user interface that the used biological indicator (700, 1200) should be removed from the sterilizing cabinet (150) and transferred to the indicator analyzer (800) so that it can be analyzed within a suitable time frame. This reminder could be enforced by, for example, a scanner within the sterilizing cabinet (152) detecting the presence of the biological indicator (700, 1200) within sterilizing chamber (152) and causing the sterilizing cabinet (150) to emit a persistent alert noise until the biological indicator (700, 1200) is removed. Once scanned (block 948) at an indicator analyzer (800), by way of identification tag reader (870) or a handheld scanner, before biological indicator (700, 1200) is placed in a well (810), or by another scanner that is able to automatically scan a variable resistance biological indicator (1200) or variable resistance biological indicator cap (1230) after a biological indicator (700, 1200) is placed in a well (810), the indicator analyzer (800) may take such steps as verifying that the biological indicator (700, 1200) matches a biological indicator (700, 1200) that it was earlier notified of (block 944), that the biological indicator (700, 1200) has been placed in or will be placed in the analyzer (800) within a suitable time frame, or that no other inconsistencies in the auditable trail of the biological indicator (700, 1200) exist (e.g. duplicate sterilization cycles).

The indicator analyzer (800) may also acknowledge (block 950) receipt of the biological indicator (700, 1200) by providing data via the network to the sterilizing cabinet (150) indicating that the biological indicator (700, 1200) was placed in the indicator analyzer (800). The sterilizing cabinet (150) could use this information to, for example, display a confirmation of proper handling of the biological indicator (700, 1200) via display (160), or prevent further alerts or alarms that might otherwise originate from the sterilizing cabinet (150) and be associated with the biological indicator (700, 1200), such as an alarm that might sound if a biological indicator (700, 1200) is not placed in an indicator analyzer (800) within one hour (or some other duration) after the biological indicator (700, 1200) is used in a sterilization cycle.

The indicator analyzer (800) may also analyze (block 952) the biological indicator (700, 1200) in order to determine whether the sterilization cycle was successful or not. Once the analysis (block 952) is complete, the indicator analyzer (800) may provide analysis results (block 954) via display (850) of the indicator analyzer (800), a network transmission of data to be displayed via display (160) of the sterilizing cabinet (150), and/or a network transmission to another device such as a smartphone, tablet, or other personal device. Such information could be used to maintain and create records of the completed sterilization cycle and biological indicator (700, 1200) used, to provide records to another device such as a records server, or to disable or prevent further notifications or alerts relating to the completed sterilization cycle or biological indicator (700, 1200). These results may also be automatically printed (block 956) via the sterilizing cabinet (150) printer (170) so that hard copies may be maintained or used for further analysis. Of course, this printing step (block 956) is merely optional and may be omitted.

Figure 10:
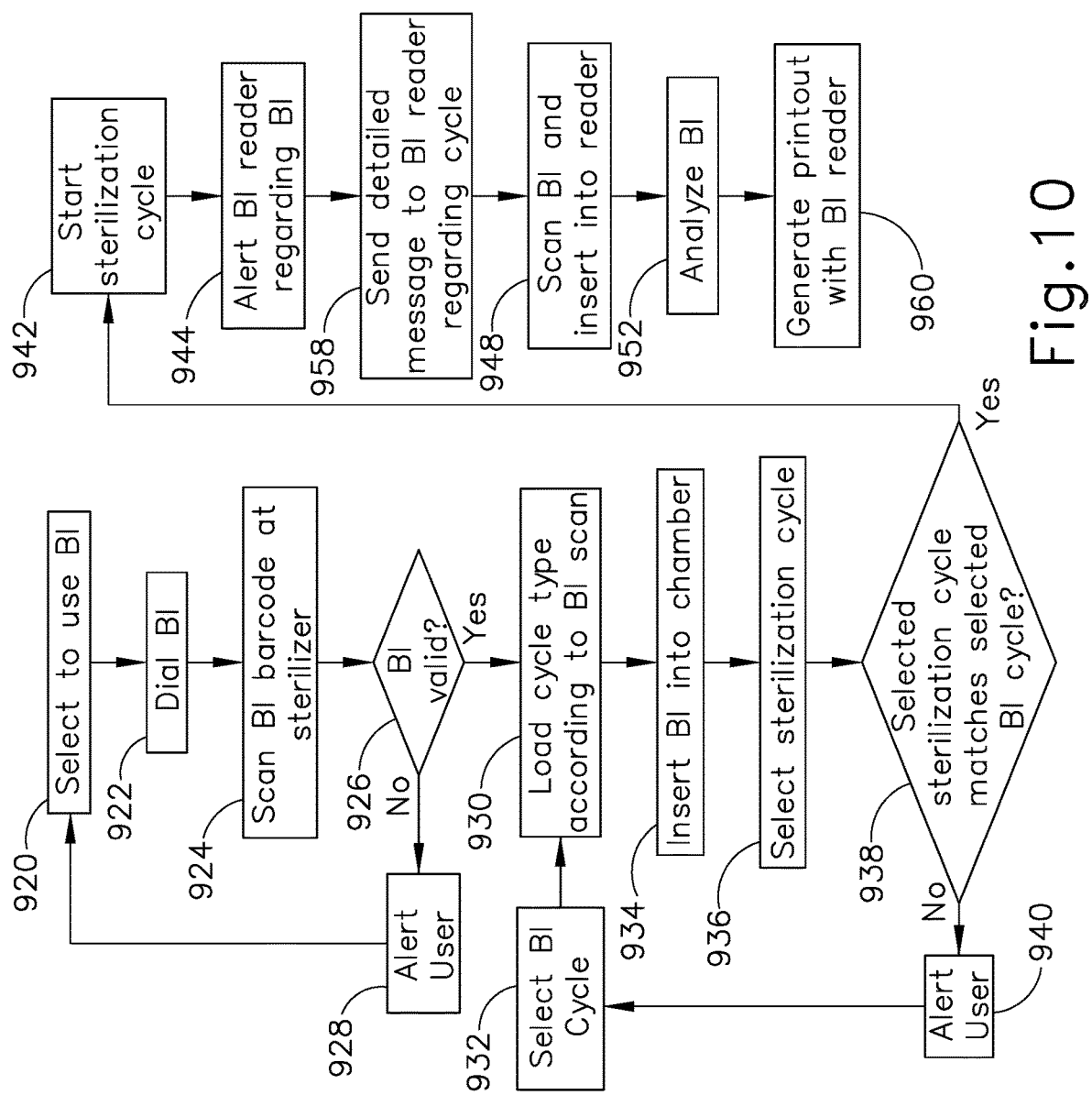
FIG. 10 depicts a flowchart of another exemplary set of steps that may be performed using a modified version of the sterilizing cabinet of FIG. 1, using a modified version of the indicator analyzer of FIG. 5, and using a modified version of the biological indicator assembly of FIG. 4.

C. Exemplary Cycle Completion with Scanner and Network with Indicator Analyzer as Master Device FIG. 10 shows a process that begins with the same set of steps (blocks 920, 922, 924, 926, 928, 930, 932, 934, 936, 938, 940) as the process of FIG. 9. Thus, discussion of those steps will not be repeated here. The remaining exemplary steps of FIG. 10, beginning after a successful determination (block 938) that a sterilization cycle selected via the sterilizing cabinet (150) matches a vent configuration selected on the variable resistance biological indicator (700, 1200), may be appropriate for a system that uses a visual scanner or wireless scanner for scanning (block 924) a variable resistance biological indicator (1200) or variable resistance biological indicator cap (1230), and which has a stable network that will allow network communication between the sterilizing cabinet (150) and the indicator analyzer (800). The exemplary steps of FIG. 10 may also show a preference for treating the indicator analyzer (800) as the master device, which may be appropriate where the indicator analyzer (800) has a dedicated user or clinician, or where the sterilizing cabinet (150) has limited ability to output information or interact with a user.

As with FIG. 9, when no errors are identified, the sterilization cycle may begin (block 942) and the indicator analyzer (800) may receive (block 944) information indicating that a particular biological indicator (700, 1200) is being used in a sterilization cycle, as has been described above. The sterilizing cabinet (150) may also provide information to the indicator analyzer (800) that provides (block 958) detailed information regarding the sterilization cycle, which could include cycle completion time, cycle pressure, cycle, temperature, load conditioning results, or other detailed information that may be used by the indicator analyzer (800) during its analysis or to maintain an auditable trail of the biological indicator (700, 1200) during the sterilization cycle.

Once the sterilization cycle is complete, the biological indicator (700, 1200) may be removed from the sterilizing cabinet (150) and scanned (block 948) and placed in a well (810) of the indicator analyzer (800) so that it can be analyzed (block 952), as has been described above. When analysis (block 952) is complete, the indicator analyzer (800) may provide information on the results of the analysis to a user or records server, and print (block 960) a hard copy of the results that may be used to maintain records or for further analysis. As noted above, this printing step (block 960) is merely optional and may be omitted if desired.

Figure 11:
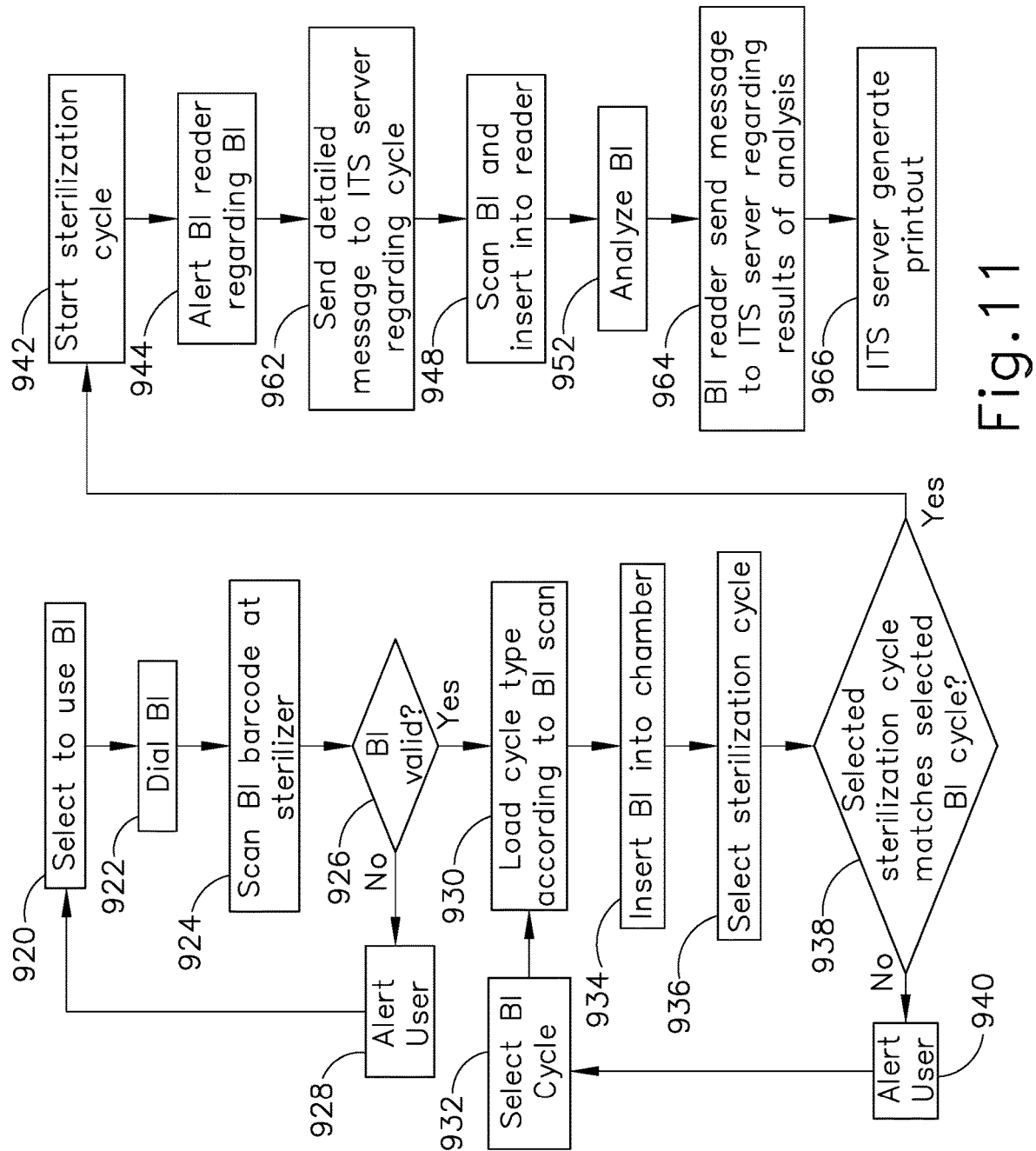
FIG. 11 depicts a flowchart of another exemplary set of steps that may be performed using a modified version of the sterilizing cabinet of FIG. 1, using a modified version of the indicator analyzer of FIG. 5, and using a modified version of the biological indicator assembly of FIG. 4.

D. Exemplary Cycle Completion with Scanner and Network with Record Server as Master FIG. 11 shows a process that begins with the same set of steps (blocks 920, 922, 924, 926, 928, 930, 932, 934, 936, 938, 940) as the process of FIG. 9. Thus, discussion of those steps will not be repeated here. The remaining exemplary steps of FIG. 11, beginning after a successful determination (block 938) that a sterilization cycle selected via the sterilizing cabinet (150) matches a vent configuration selected on the variable resistance biological indicator (700, 1200), may be appropriate for a system that uses a visual scanner or wireless scanner for scanning (block 924) a variable resistance biological indicator (1230) or variable resistance biological indicator cap (1230), and which has a stable network that will allow network communication between the sterilizing cabinet (150), the indicator analyzer (800), and a record server. The exemplary steps of FIG. 11 may also show a preference for treating an external record server (not shown) as the master device, which may be appropriate where the record server serves a role of monitoring sterilization cycles and biological indicator use, or where the sterilizing cabinet (150) and/or indicator analyzer (800) have limited ability to output information or interact with a user.

As with FIG. 9, when no errors are identified the sterilization cycle may begin (block 942) and the indicator analyzer (800) may receive (block 944) information indicating that a particular biological indicator (700, 1200) is being used in a sterilization cycle, as has been described above. In the exemplary steps shown, the sterilizing cabinet (150) may send (block 962) detailed information on the sterilization cycle to the record server, which may include information such as sterilization cycle identifier, sterilizing cabinet identifier (150), user identifier, start time, end time, biological indicator (700, 1200) identifier, lot number, cycle details such as pressure, temperature, load type, or other information generated and associated with a sterilization cycle that may be pertinent to monitoring the performance of sterilization cycles or maintaining an auditable trail of information for cycles and biological indicators (700, 1200).

When the sterilization cycle completes, a user may remove the biological indicator (700, 1200) from the sterilizing cabinet (150) so that the biological indicator (700, 1200) can be scanned (block 948) and placed in a well (810) of the indicator analyzer (800) and the results of the sterilization cycle can be analyzed (block 952), as has been described above. The indicator analyzer (800) may send (block 964) results information to the record server, which may be used by a user of the records server to monitor the results of one or more sterilization cycles or biological indicator (700, 1200) analyses; or may be used to maintain records relating to the performance of cycles and analysis of biological indicators (700, 1200). The record server may print (block 966) some or all of the information provided so that it can be maintained in hard copy or used for further analysis. As noted above, this printing step (block 966) is merely optional and may be omitted if desired.

Figure 12:
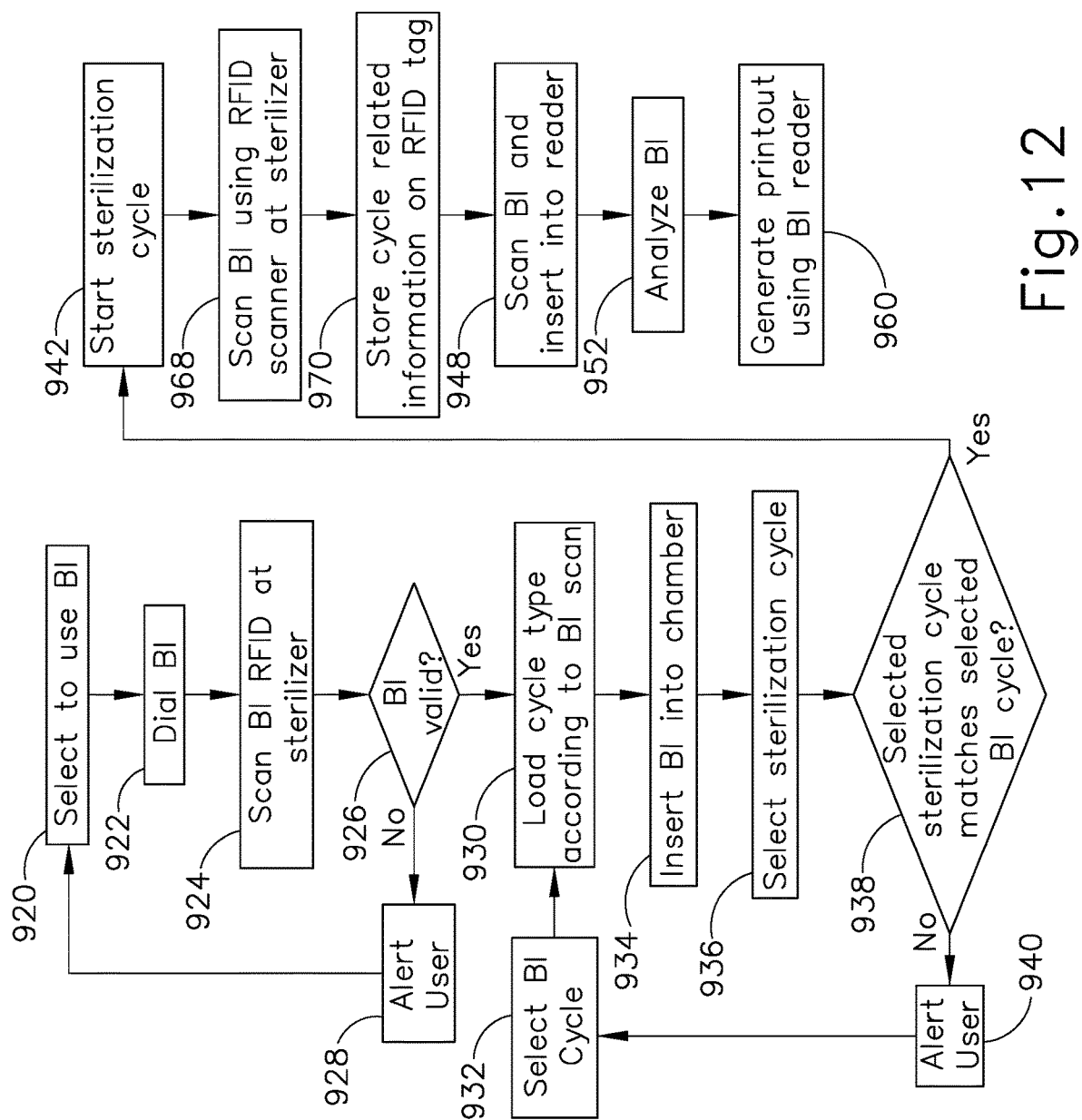
FIG. 12 depicts a flowchart of another exemplary set of steps that may be performed using a modified version of the sterilizing cabinet of FIG. 1, using a modified version of the indicator analyzer of FIG. 5, and using a modified version of the biological indicator assembly of FIG. 4.

E. Exemplary Cycle Completion with Scanner, Writer, and Indicator Analyzer as Master FIG. 12 shows a process that begins with the same set of steps (blocks 920, 922, 924, 926, 928, 930, 932, 934, 936, 938, 940) as the process of FIG. 9. Thus, discussion of those steps will not be repeated here. The remaining exemplary steps of FIG. 12, beginning after a successful determination (block 938) that a sterilization cycle selected via the sterilizing cabinet (150) matches a vent configuration selected on the variable resistance biological indicator (700, 1200), may be appropriate for a system that uses a wireless scanner that is capable of scanning (block 924) information from and writing data to a wireless memory such as an RFID or NFC chip of a variable resistance biological indicator (1200) or variable resistance biological indicator cap (1230), with or without a network providing communications between the sterilizing cabinet (150) and the indicator analyzer (800). The exemplary steps of FIG. 12 may also show a preference for treating the indicator analyzer (800) as the master device, which may be appropriate where there is no network connectivity between the indicator analyzer (800) and the sterilizing cabinet (150) that will readily allow the indicator analyzer (800) to notify the sterilizing cabinet (800) of the results of an analysis.

As with FIG. 9, when no errors are identified the sterilization cycle may begin (block 942). Since the exemplary steps of FIG. 12 do not rely on network connectivity between the sterilizing cabinet (150) and the indicator analyzer (800), there may not be a direct exchange of cycle information between the devices. Instead, a user with a handheld scanner, or the sterilizing cabinet (150) using a short range scanner (e.g., identification tag reader (166)), may scan (block 968) a machine readable indicator of the biological indicator (700, 1200) and write sterilization cycle information to the machine readable indicator (1212, 1218, 1222, 1226) where it may be stored (block 970).

After the sterilization cycle is complete, a user may remove the biological indicator (700, 1200) from sterilizing cabinet (150) and transport biological indicator (700, 1200) to the indicator analyzer (800) where biological indicator (700, 1200) may be scanned (block 948). In addition to information that may have been present on a machine readable indicator (1212, 1218, 1222, 1226) of the biological indicator (700, 1200) prior to use of biological indicator (700, 1200) in sterilizing cabinet (150), such as a biological indicator (700, 1200) identifier, expiration date, or other similar information, the machine readable indicator (1212, 1218, 1222, 1226) may also now contain sterilization cycle related information that was stored (block 970) there by the sterilizing chamber (150). In effect, this allows for updated information to be transported directly on biological indicator (700, 1200), between the sterilizing cabinet (150) and the indicator analyzer (800), during physical transportation of the biological indicator (700, 1200) to the well (810), rather than by reliance on network communications. The indicator analyzer (800) may also perform analyses (block 952) of the biological indicator (700, 1200) and print (block 960) the results, as has been described above.

F. Exemplary Cycle Completion with Automated Variable Resistance Configuration

Figure 13:
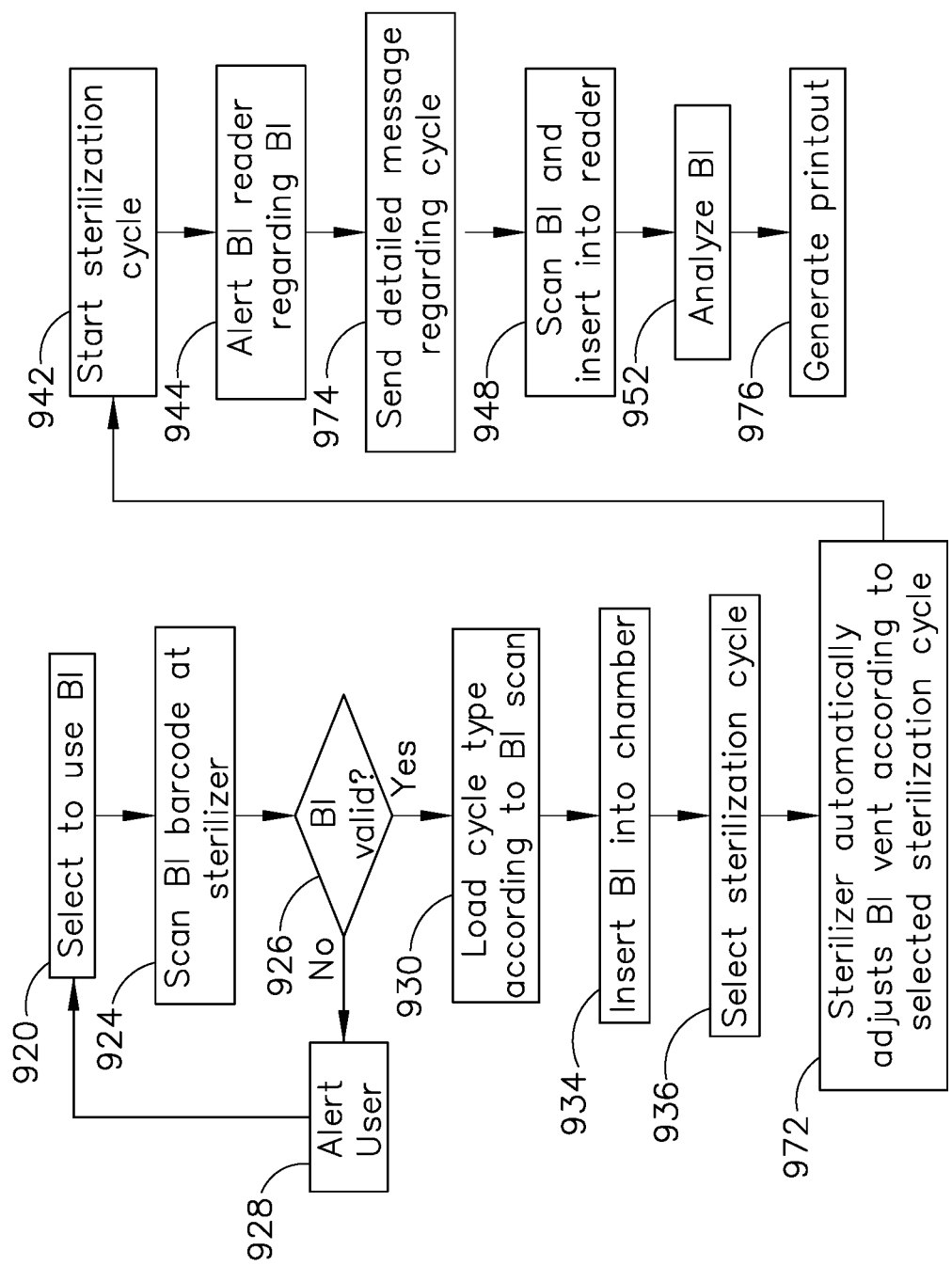
FIG. 13 depicts a flowchart of another exemplary set of steps that may be performed using a modified version of the sterilizing cabinet of FIG. 1, using a modified version of the indicator analyzer of FIG. 5, and using a modified version of the biological indicator assembly of FIG. 4.

FIG. 13 shows a process that begins with several of the same steps (blocks 920, 924, 926, 928, 930, 934, 936) as the process of FIG. 9. Thus, discussion of those steps will not be repeated here. It should be noted that the process of FIG. 13 in particular does not require a user to select (block 922) a vent configuration before placing (block 934) the biological indicator (700, 1200) in the sterilizing cabinet (150) and selecting (block 936) the sterilization cycle. The process of FIG. 13 may be appropriate for a system having a sterilizing cabinet (150) that is capable of automatically rotating a cap (1202, 1230) or housing (710, 1206) of a variable resistance biological indicator through the use of a rotatable or otherwise movable gripping device and biological indicator holder incorporated with the sterilizing cabinet (150). With such a sterilizing cabinet, if a mismatch was identified, the sterilizing cabinet (150) could deploy a rotatable gripping or moving device to grip the cap (1202, 1230) or housing (710, 1206) of the biological indicator while a biological indicator holder within the sterilizing cabinet immobilizes the non-rotating portion of the biological indicator (700, 1200). Once gripped, the cap (1202, 1230) or housing (710, 1206) could be automatically rotated, adjusted, or otherwise manipulated (block 972) until the sterilizing cabinet (150) is able to locate a machine readable indicator (1212, 1218, 1222, 1226) on the variable resistance biological indicator cap (1230) or variable resistance biological indicator (1200) that matches the selected cycle. Such an implementation may be useful in preventing time consuming adjustments of biological indicators (700, 1200) after a sterilizing cabinet (150) has already been sealed and prepared for a sterilization cycle, and may also reduce human error in configuring variable resistance biological indicators (700, 1200).

Once the variable resistance biological indicator (1200) or variable resistance biological indicator cap (1230) is adjusted to the appropriate position and vent configuration, the sterilization cycle may begin (block 942), with information being sent (block 944) to the indicator analyzer (800) as described above, and detailed messages being sent (block 974) to a sterilizing cabinet (150) or record server as may be appropriate. Once the sterilization cycle is complete, the biological indicator may be removed from the sterilizing cabinet (150) and transported to the indicator analyzer (800) where it may be scanned (block 948) and inserted for analysis (block 952) as has been described above. Once analysis is complete, notifications may be generated and the results printed (block 976) on whichever device is being treated as a master device for that particular implementation.

VII. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A system, comprising: (a) a sterilizing cabinet comprising a sterilizing chamber and a user interface; (b) a biological indicator analyzer comprising at least one biological indicator receiver; and (c) a variable resistance biological indicator comprising: (i) a set of readable indicators, the set of readable indicators comprising a first readable indicator and a second readable indicator, (ii) an indicator window, and (iii) an adjustable portion operable to selectively move between selected vent positions from a set of vent positions, the set of vent positions comprising a first vent position and a second vent position, wherein each readable indicator of the set of readable indicators is associated with a corresponding vent position of the set of vent positions, wherein the adjustable portion is configured to position first readable indicator in the indicator window when the adjustable portion is in the first vent position; wherein the biological indicator analyzer is configured to detect one or more microorganisms in the biological indicator; wherein the sterilizing cabinet is configured to execute instructions to verify, based upon the first readable indicator, that the first vent position is compatible with a selected sterilization cycle before the selected sterilization cycle begins.

Example 2

The system of Example 1, wherein the adjustable portion of the variable resistance biological indicator comprises an inner layer and an outer layer; wherein the adjustable portion comprises a rotatable portion; wherein the indicator window is positioned on the outer layer; wherein the set of readable indicators are fixed to the inner layer; wherein the inner layer remains in a fixed position relative to the outer layer when the rotatable portion is rotated; wherein the indicator window is positioned so that at most one readable indicator is within the indicator window at any time.

Example 3

The system of Example 2, wherein the adjustable portion comprises a cap of the variable resistance biological indicator.

Example 4

The system of any one or more of Examples 2 through 3, wherein the adjustable portion comprises a housing of the variable resistance biological indicator.

Example 5

The system of any one or more of Examples 1 through 4, wherein the user interface comprises a touch screen display; wherein the sterilizing cabinet further comprises a machine readable indicator scanner, wherein the machine readable indicator scanner comprises a type selected from the group consisting of a barcode scanner, a data matrix code scanner, a QR code scanner, an RFID scanner, and a NFC scanner; wherein each indicator of the set of readable indicators comprises a type selected from the group consisting of a barcode, a data matrix code, a QR code, an RFID chip, and a NFC chip; wherein the set of indicator data comprises two or more of: (i) a biological indicator identifier, (ii) a biological indicator expiration date, (iii) a biological indicator manufacturer, (iv) a biological indicator cycle type and vent position, or (v) a previous use indicator.

Example 6

The system of any one or more of Examples 1 through 5, wherein the biological indicator analyzer further comprises an analyzer scanner, wherein the sterilizing cabinet is further configured to, after the start of a sterilization cycle, execute instructions to: (i) provide a cycle start record to the biological indicator analyzer, and (ii) after the sterilization cycle is complete, provide a biological indicator reminder to the user; and wherein the biological indicator analyzer is configured to execute instructions to: (i) capture the set of indicator data from the first readable indicator via the analyzer scanner, (ii) provide an analysis start record to the sterilizing cabinet, (iii) perform an analysis of the variable resistance biological indicator to determine a result of the sterilization cycle, and (iv) provide the result to the sterilizing cabinet.

Example 7

The system of any one or more of Examples 1 through 6, wherein the biological indicator analyzer further comprises an analyzer scanner, wherein the sterilizing cabinet is further configured to, after the start of a sterilization cycle, execute instructions to (i) provide a cycle start record to the biological indicator analyzer, and (ii) after the sterilization cycle is complete, provide a biological indicator reminder to the user and provide a cycle completion record to the biological indicator analyzer; and wherein the biological indicator analyzer is configured to execute instructions to: (i) capture the set of indicator data from the first readable indicator via the analyzer scanner, and (ii) perform an analysis of the variable resistance biological indicator to determine a result of the sterilization cycle.

Example 8

The system of any one or more of Examples 1 through 7, wherein the sterilizing cabinet further comprises a readable indicator scanner, wherein the readable indicator scanner comprises a passive tag communicator; wherein the variable resistance biological indicator comprises an electromagnetic shield layer, wherein the electromagnetic shield layer is configured to mitigate communication between the passive tag communicator and every readable indicator of the set of readable indicators not within the indicator window; wherein the biological indicator analyzer further comprises an analyzer passive tag communicator; wherein the sterilizing cabinet is further configured to, after completing a sterilization cycle, execute instructions to store a cycle completion record on a memory of the first readable indicator using the passive tag communicator; wherein the biological indicator analyzer is configured to execute instructions to: (i) capture the set of indicator data from the first readable indicator via the analyzer passive tag communicator, (ii) capture the cycle completion record from the first readable indicator via the analyzer passive tag communicator, and (iii) perform an analysis of the variable resistance biological indicator to determine a result of the sterilization cycle.

Example 9

The system of any one or more of Examples 1 through 8, further comprising a record server, wherein the biological indicator analyzer further comprises an analyzer scanner, wherein the sterilizing cabinet is further configured to, after the start of a sterilization cycle, execute instructions to: (i) provide a cycle start record to the biological indicator analyzer, and (ii) after the sterilization cycle is complete, provide a biological indicator reminder to the user and provide a cycle completion record to the record server; and wherein the biological indicator analyzer is configured to execute instructions to: (i) capture the set of indicator data from the first readable indicator via the analyzer scanner, (ii) perform an analysis of the variable resistance biological indicator to determine a result of the sterilization cycle, and (iii) provide the result to the record server.

Example 10

The system of any one or more of Examples 1 through 9, wherein the sterilizing cabinet further comprises a biological indicator holder and a biological indicator adjustor, wherein the biological indicator adjustor is operable to selectively adjust the adjustable vent of a biological indicator held by the biological indicator holder; wherein the sterilizing cabinet is further configured to execute instructions to, when the selected sterilization cycle is not within the set of supported sterilization cycles: (i) determine a second vent position associated with a second set of supported sterilization cycles, wherein the selected sterilization cycle is within the second set of supported sterilization cycles, (ii) operate the adjustable vent of the variable resistance biological indicator to the second vent position, and (iii) begin the selected sterilization cycle.

Example 11

The system of any one or more of Examples 1 through 10, wherein the sterilizing cabinet is further configured to execute instructions to only begin the selected sterilization cycle when the set of indicator data indicates that: (i) the variable resistance biological indicator is not expired, and (ii) the variable resistance biological indicator is from an approved manufacturer.

Example 12

The system of any one or more of Examples 1 through 11, wherein the sterilizing cabinet further comprises a readable indicator scanner, wherein the readable indicator scanner comprises a passive tag communicator; wherein the passive tag communicator is positioned to scan the contents of the sterilizing chamber; and wherein the sterilizing cabinet is further configured to execute instructions to: (i) capture a set of indicator data from the first readable indicator via the readable indicator scanner automatically after the variable resistance biological indicator is placed within the sterilizing chamber, (ii) determine if the variable resistance biological indicator has been used in a previous sterilization cycle based upon the set of indicator data, (iii) only begin the selected sterilization cycle when the variable resistance biological indicator has not been used in a previous sterilization cycle, and (iv) after the selected sterilization cycle begins, update the set of indicator data on the first readable indicator via the passive tag communicator to reflect that the variable resistance biological indicator has been used in a previous sterilization cycle.

Example 13

The system of Example 12, wherein the sterilizing cabinet is not communicatively coupled with another device over a network.

Example 14

The system of any one or more of Examples 1 through 13, wherein the sterilizing cabinet further comprises a readable indicator scanner, wherein the instructions to verify that the first vent position is compatible with a selected sterilization cycle before the selected sterilization cycle begins comprise instructions that, when executed, cause the sterilizing cabinet to: (i) capture a set of indicator data from the first readable indicator via the readable indicator scanner, (ii) determine that the variable resistance biological indicator is at the first vent position based upon the set of indicator data, (iii) identify a set of supported sterilization cycles that are associated with the first vent position, (iv) receive, from a user via the user interface, the selected sterilization cycle, (v) when the selected sterilization cycle is within the set of supported sterilization cycles, begin the selected sterilization cycle, and (vi) when the selected sterilization cycle is not within the set of supported sterilization cycles, provide an indication that the selected sterilization cycle is not within the set of supported sterilization cycles.

Example 15

The system of Example 14, wherein the set of indicator data is encrypted, and wherein the sterilizing cabinet is further configured to execute instructions to decrypt the set of indicator data.

Example 16

A method comprising the steps: (a) capturing a set of indicator data relating to a vent position of a variable resistance biological indicator via a sterilizing cabinet; (b) determining, via the sterilizing cabinet, that the variable resistance biological indicator is at a first vent position based upon the set of indicator data; (c) identifying a set of supported sterilization cycles that are associated with the first vent position; (d) receiving the variable resistance biological indicator in a sterilizing chamber of the sterilizing cabinet; (e) receiving a selected sterilization cycle via a user interface of the sterilizing cabinet; and (f) either: (i) when the selected sterilization cycle is within the set of supported sterilization cycles, beginning the selected sterilization cycle, or (ii) when the selected sterilization cycle is not within the set of supported sterilization cycles, providing an indication that the selected sterilization cycle is not within the set of supported sterilization cycles; wherein the variable resistance biological indicator comprises an indicator window, an adjustable portion, and at least two vent indicators, and wherein the adjustable portion is adapted to be adjusted to a first position which causes the first vent indicator to be detectable through the indicator window and causes the variable resistance biological indicator to be in the first vent position.

Example 17

The method of Example 16, further comprising the steps: (a) after beginning a sterilization cycle, providing a cycle start record from the sterilizing cabinet to a biological indicator analyzer; (b) after completing the sterilization cycle, providing a biological indicator reminder; (c) at the biological indicator analyzer, capturing the set of indicator data from the first readable indicator via an analyzer scanner of the biological indicator analyzer; (d) providing an analysis start record from the biological indicator analyzer to the sterilizing cabinet; (e) performing an analysis of the variable resistance biological indicator to determine a result of the sterilization cycle; and (f) providing the result to the sterilizing cabinet.

Example 18

The method of any one or more of Examples 16 through 17, further comprising the steps: (a) after completing a sterilization cycle, storing a cycle completion record on a memory of the first readable indicator via a passive tag communicator; (b) capturing the set of indicator data from the first readable indicator via the passive tag communicator; (c) capturing the cycle completion record from the first readable indicator via the passive tag communicator; and (d) performing an analysis of the variable resistance biological indicator to determine a result of the sterilization cycle.

Example 19

The method of any one or more of Examples 16 through 18, wherein the set of indicator data is captured automatically after the variable resistance biological indicator is placed within the sterilizing chamber, the method further comprising: (a) determining if the variable resistance biological indicator has been used in a previous sterilization cycle based upon the set of indicator data; (b) only beginning the selected sterilization cycle when the variable resistance biological indicator has not been used in a previous sterilization cycle; and (c) after beginning the selected sterilization cycle, updating the set of indicator data on the first readable indicator via a passive tag communicator to reflect that the variable resistance biological indicator has been used in a previous sterilization cycle.

Example 20

A system comprising: (a) a sterilizing cabinet comprising a sterilizing chamber, a user interface, and a first tag communicator; (b) a biological indicator analyzer comprising at least one biological indicator receiver and a second tag communicator, wherein the sterilizing cabinet and the biological indicator analyzer are not communicatively coupled by a network; and (c) a means for adjusting the resistance of a biological indicator and transporting information between devices.

VIII. MISCELLANEOUS

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings. Instead, the protection should be understood to be defined by the claims, if any, set forth herein or in the relevant related document when the terms in those claims which are listed below under the label "Explicit Definitions" are given the explicit definitions set forth therein, and the remaining terms are given their broadest reasonable interpretation as shown by a general purpose dictionary.

To the extent that the interpretation which would be given to such claims based on the above disclosure is in any way narrower than the interpretation which would be given based on the "Explicit Definitions" and the broadest reasonable interpretation as provided by a general purpose dictionary, the interpretation provided by the "Explicit Definitions" and broadest reasonable interpretation as provided by a general purpose dictionary shall control, and the inconsistent usage of terms in the specification or priority documents shall have no effect. For flowcharts or step diagrams that are shown or described as being serial, it should be understood that the steps may instead be performed in parallel unless such an implementation is specifically disclaimed or inherently impossible due to stated dependencies. Likewise, any flowchart or step diagram that is shown or described as being parallel may instead be performed in series or in sequence, unless such an implementation is specifically disclaimed or inherently impossible due to stated dependencies. When used in the figures and written description the terms select, selection, selected, and other variations may not refer to specific technologies, database syntax, or programming languages, and instead refer to a more general process of querying, searching, or identifying a matching or partially matching data set from a larger pool of data.

Explicit Definitions

When appearing in the claims, a statement that something is "based on" something else should be understood to mean that something is determined at least in part by the thing that it is indicated as being "based on." When something is required to be completely determined by a thing, it will be described as being "based exclusively on" the thing.

When used in the claims, "configured" should be understood to mean that the thing "configured" is adapted, designed or modified for a specific purpose. An example of "configuring" in the context of computers is to provide a computer with specific data (which may include instructions) which can be used in performing the specific acts the computer is being "configured" to do. For example, installing Microsoft® WORD on a computer "configures" that computer to function as a word processor, which it does by using the instructions for Microsoft WORD in combination with other inputs, such as an operating system, and various peripherals (e.g., a keyboard, monitor, etc).

When used in the claims, "determining" should be understood to refer to generating, selecting, defining, calculating or otherwise specifying something. For example, to obtain an output as the result of analysis would be an example of "determining" that output. As a second example, to choose a response from a list of possible responses would be a method of "determining" a response. As a third example, to identify data received from an external source (e.g., a microphone) as being a thing would be an example of "determining" the thing.

When used in the claims, a "means for adjusting the resistance of a biological indicator transporting information between devices" should be understood as a limitation set forth in the form of a means for performing a specified function as provided for in the sixth paragraph of 35 U.S.C. § 112 in which the specified function is adjusting the resistance of a biological indicator and transporting information between devices as described in FIG. 12 and its related discussion, and the corresponding structure is a system having physical components such as biological indicators shown in FIGS. 7A-7B, and 8A-8C, and their related discussions.

When used in the claims, a "set" should be understood to refer to a collection containing zero or more objects of the type that it refers to. So, for example, a "set of integers" describes an object configured to contain an integer value, which includes an object that contains multiple integer values, an object that contains only a single integer value, and an object that contains no integer value whatsoever.

We claim:

1. A system comprising:
   (a) a sterilizing cabinet comprising a sterilizing chamber, a user interface, and a first tag communicator;
   (b) a biological indicator analyzer comprising at least one biological indicator receiver and a second tag communicator, wherein the sterilizing cabinet and the biological indicator analyzer are not communicatively coupled by a network;
   (c) a means for adjusting a resistance of a biological indicator; and
   (d) a means for transporting information between the sterilizing cabinet and the biological indicator.

2. A system, comprising:
   (a) a sterilizing cabinet comprising a sterilizing chamber and a user interface;
   (b) a biological indicator analyzer; and
   (c) a variable resistance biological indicator comprising:
      (i) a set of readable indicators, the set of readable indicators comprising a first readable indicator and a second readable indicator,
      (ii) an indicator window, and
      (iii) an adjustable portion operable to selectively move between a selected vent positions from a set of vent positions, the set of vent positions comprising a first vent position and a second vent position, wherein the first readable indicator is associated with the first vent position and the second readable indicator is associated with the second vent position,
      wherein the adjustable portion is configured to position the first readable indicator in the indicator window when the adjustable portion is in the first vent position based on a set of indicator data from the sterilizing cabinet;
   wherein the sterilizing cabinet is configured to identify a set of supported sterilization cycles associated with the first vent position and receive a selected sterilization cycle via the user interface, and wherein the sterilization cabinet is configured to execute instructions to verify that the selected sterilization cycle is within the set of supported sterilization cycles before the selected sterilization cycle begins.

3. The system of claim 2, wherein an analyzer scanner of the biological indicator analyzer is configured to capture the set of indicator data from the first readable indicator after the completion of a sterilization cycle, and wherein the biological indicator analyzer is configured to provide the result of the sterilization cycle to the sterilizing cabinets based on the set of indicator data from the first readable indicator.

4. The system of claim 2, further comprising a passive tag communicator configured to store a cycle completion record on a memory of the first readable indicator after a sterilization cycle ends, wherein the passive tag communicator is further configured to capture the set of indicator data from the first readable indicator and the cycle completion record, and wherein the variable resistance biological indicator is analyzed to determine a result of the sterilization cycle.

5. A system, comprising:
   (a) a sterilizing cabinet comprising a sterilizing chamber and a user interface;
   (b) a biological indicator analyzer comprising at least one biological indicator receiver; and
   (c) a variable resistance biological indicator comprising:
      (i) a set of readable indicators, the set of readable indicators comprising a first readable indicator and a second readable indicator,
      (ii) an indicator window, and
      (iii) an adjustable portion operable to selectively move between selected vent positions from a set of vent positions, the set of vent positions comprising a first vent position and a second vent position, wherein the first readable indicator is associated with the first vent position and the second readable indicator is associated with the second vent position,
      wherein the adjustable portion is configured to position the first readable indicator in the indicator window when the adjustable portion is in the first vent position;
   wherein the biological indicator analyzer is configured to detect one or more microorganisms in the variable resistance biological indicator;
   wherein the sterilizing cabinet is configured to execute instructions to verify, based upon the first readable indicator, that the first vent position is compatible with a selected sterilization cycle before the selected sterilization cycle begins.

6. The system of claim 5, wherein the adjustable portion of the variable resistance biological indicator comprises an inner layer and an outer layer;
   wherein the adjustable portion comprises a rotatable portion;
   wherein the indicator window is positioned on the outer layer;
   wherein the set of readable indicators are fixed to the inner layer;
   wherein the inner layer remains in a fixed position relative to the outer layer when the rotatable portion is rotated;
   wherein the indicator window is positioned so that at most one readable indicator is within the indicator window at any time.

7. The system of claim 6, wherein the adjustable portion comprises a cap of the variable resistance biological indicator.

8. The system of claim 6, wherein the adjustable portion comprises a housing of the variable resistance biological indicator.

9. The system of claim 5, wherein the user interface comprises a touch screen display;
   wherein the sterilizing cabinet further comprises a machine readable indicator scanner, wherein the machine readable indicator scanner comprises a type selected from the group consisting of a barcode scanner, a data matrix code scanner, a QR code scanner, an RFID scanner, and a NFC scanner;
   wherein each readable indicator of the set of readable indicators comprises a type selected from the group consisting of a barcode, a data matrix code, a QR code, an RFID chip, and a NFC chip;
   wherein a set of indicator data comprises two or more of:
      (i) a biological indicator identifier,
      (ii) a biological indicator expiration date,
      (iii) a biological indicator manufacturer,
      (iv) a biological indicator cycle type and vent position, or
      (v) a previous use indicator.

10. The system of claim 5, wherein the biological indicator analyzer further comprises an analyzer scanner, wherein the sterilizing cabinet is further configured to, after the start of a sterilization cycle, execute instructions to:
   (i) provide a cycle start record to the biological indicator analyzer, and
   (ii) after the sterilization cycle is complete, provide a biological indicator reminder to a user; and wherein the biological indicator analyzer is configured to execute instructions to:
(i) capture a set of indicator data from the first readable indicator via the analyzer scanner,
(ii) provide an analysis start record to the sterilizing cabinet,
(iii) perform an analysis of the variable resistance biological indicator to determine a result of the sterilization cycle, and
(iv) provide the result to the sterilizing cabinet.

11. The system of claim 5, wherein the biological indicator analyzer further comprises an analyzer scanner, wherein the sterilizing cabinet is further configured to, after the start of a sterilization cycle, execute instructions to:
(i) provide a cycle start record to the biological indicator analyzer, and
(ii) after the sterilization cycle is complete, provide a biological indicator reminder to a user and provide a cycle completion record to the biological indicator analyzer; and
wherein the biological indicator analyzer is configured to execute instructions to:
(i) capture a set of indicator data from the first readable indicator via the analyzer scanner, and
(ii) perform an analysis of the variable resistance biological indicator to determine a result of the sterilization cycle.

12. The system of claim 5, wherein the sterilizing cabinet further comprises a readable indicator scanner, wherein the readable indicator scanner comprises a passive tag communicator;
wherein the variable resistance biological indicator comprises an electromagnetic shield layer, wherein the electromagnetic shield layer is configured to mitigate communication between the passive tag communicator and every readable indicator of the set of readable indicators not within the indicator window;
wherein the biological indicator analyzer further comprises an analyzer passive tag communicator;
wherein the sterilizing cabinet is further configured to, after completing a sterilization cycle, execute instructions to store a cycle completion record on a memory of the first readable indicator using the passive tag communicator;
wherein the biological indicator analyzer is configured to execute instructions to:
(i) capture a set of indicator data from the first readable indicator via the analyzer passive tag communicator,
(ii) capture the cycle completion record from the first readable indicator via the analyzer passive tag communicator, and
(iii) perform an analysis of the variable resistance biological indicator to determine a result of the sterilization cycle.

13. The system of claim 5, further comprising a record server, wherein the biological indicator analyzer further comprises an analyzer scanner, wherein the sterilizing cabinet is further configured to, after the start of a sterilization cycle, execute instructions to:
(i) provide a cycle start record to the biological indicator analyzer, and
(ii) after the sterilization cycle is complete, provide a biological indicator reminder to a user and provide a cycle completion record to the record server; and
wherein the biological indicator analyzer is configured to execute instructions to:
(i) capture a set of indicator data from the first readable indicator via the analyzer scanner,
(ii) perform an analysis of the variable resistance biological indicator to determine a result of the sterilization cycle, and
(iii) provide the result to the record server.

14. The system of claim 5, wherein the sterilizing cabinet further comprises a biological indicator holder and a biological indicator adjustor, wherein the biological indicator adjustor is operable to selectively adjust the adjustable portion of the variable resistance biological indicator held by the biological indicator holder;
wherein the sterilizing cabinet is further configured to execute instructions to, when the selected sterilization cycle is not within a set of supported sterilization cycles:
(i) determine the second vent position associated with a second set of supported sterilization cycles, wherein the selected sterilization cycle is within the second set of supported sterilization cycles,
(ii) operate the adjustable portion of the variable resistance biological indicator to the second vent position, and
(iii) begin the selected sterilization cycle.

15. The system of claim 5, wherein the sterilizing cabinet is further configured to execute instructions to only begin the selected sterilization cycle when a set of indicator data indicates that:
(i) the variable resistance biological indicator is not expired, and
(ii) the variable resistance biological indicator is from an approved manufacturer.

16. The system of claim 5, wherein the sterilizing cabinet further comprises a readable indicator scanner, wherein the readable indicator scanner comprises a passive tag communicator;
wherein the passive tag communicator is positioned to scan the contents of the sterilizing chamber; and
wherein the sterilizing cabinet is further configured to execute instructions to:
(i) capture a set of indicator data from the first readable indicator via the readable indicator scanner automatically after the variable resistance biological indicator is placed within the sterilizing chamber,
(ii) determine if the variable resistance biological indicator has been used in a previous sterilization cycle based upon the set of indicator data,
(iii) only begin the selected sterilization cycle when the variable resistance biological indicator has not been used in a previous sterilization cycle, and
(iv) after the selected sterilization cycle begins, update the set of indicator data on the first readable indicator via the passive tag communicator to reflect that the variable resistance biological indicator has been used in a previous sterilization cycle.

17. The system of claim 16, wherein the sterilizing cabinet is not communicatively coupled with another device over a network.

18. The system of claim 5, wherein the sterilizing cabinet further comprises a readable indicator scanner, wherein the instructions to verify that the first vent position is compatible with a selected sterilization cycle before the selected sterilization cycle begins comprise instructions that, when executed, cause the sterilizing cabinet to:
(i) capture a set of indicator data from the first readable indicator via the readable indicator scanner, (ii) determine that the variable resistance biological indicator is at the first vent position based upon the set of indicator data,
(iii) identify a set of supported sterilization cycles that are associated with the first vent position,
(iv) receive, from a user via the user interface, the selected sterilization cycle,
(v) when the selected sterilization cycle is within the set of supported sterilization cycles, begin the selected sterilization cycle, and
(vi) when the selected sterilization cycle is not within the set of supported sterilization cycles, provide an indication that the selected sterilization cycle is not within the set of supported sterilization cycles.

19. The system of claim 18, wherein the set of indicator data is encrypted, and wherein the sterilizing cabinet is further configured to execute instructions to decrypt the set of indicator data.

\* \* \* \* \*